(12) United States Patent
Takahashi et al.

(10) Patent No.: US 8,212,861 B2
(45) Date of Patent: Jul. 3, 2012

(54) MEDICAL APPARATUS

(75) Inventors: Misa Takahashi, Hachioji (JP); Nobuyoshi Yazawa, Hachioji (JP); Sho Nakajima, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/177,645

(22) Filed: Jul. 7, 2011

(65) Prior Publication Data

US 2012/0050511 A1 Mar. 1, 2012

Related U.S. Application Data

(63) Continuation of application No. PCT/JP2011/058889, filed on Apr. 8, 2011.

(30) Foreign Application Priority Data

Aug. 25, 2010 (JP) .................................. 2010-188636

(51) Int. Cl.
*H04N 7/18* (2006.01)
(52) U.S. Cl. ........................................... 348/65; 348/61
(58) Field of Classification Search ..................... 348/61, 348/65
See application file for complete search history.

(56) References Cited

U.S. PATENT DOCUMENTS

| 2008/0312499 | A1 | 12/2008 | Handa et al. |
|---|---|---|---|
| 2009/0299137 | A1 | 12/2009 | Gal et al. |
| 2009/0322864 | A1 | 12/2009 | Karasawa et al. |
| 2010/0036199 | A1 | 2/2010 | Karasawa et al. |
| 2010/0076259 | A1 | 3/2010 | Asada et al. |

FOREIGN PATENT DOCUMENTS

| JP | H03-98803 | 10/1991 |
|---|---|---|
| JP | 2002-204773 | 7/2002 |
| JP | 2007-020951 | 2/2007 |
| JP | 2008-307225 | 12/2008 |
| JP | 2009-072367 | 4/2009 |
| JP | 2010-005338 | 1/2010 |
| JP | 2010-012222 | 1/2010 |
| JP | 2010-035825 | 2/2010 |
| JP | 2010-069094 | 4/2010 |
| WO | 2007/078003 A1 | 7/2007 |
| WO | 2007/138567 A2 | 12/2007 |

*Primary Examiner* — Allen Wong
(74) *Attorney, Agent, or Firm* — Scully, Scott, Murphy & Presser, P.C.

(57) ABSTRACT

A medical apparatus includes: an image pickup apparatus introduced and retained in a body; a retaining/fixing section which contacts a body wall in the body, for retaining and fixing the image pickup apparatus at the body wall; plural operation wires operated from an extracorporeal side; and an observation direction control section which changes an observation direction of the image pickup apparatus by operation of the plural wires, and includes: an image pickup apparatus fixing section connected to the operation wires, which contacts an outer surface part of the image pickup apparatus; and a rotary section for supporting the retaining/fixing section and the image pickup apparatus fixing section so as to be separated from each other by a predetermined distance, and allowing the image pickup apparatus fixing section to rotate with respect to the retaining/fixing section with a rotation center as a fulcrum, based on operation of the plural operation wires.

6 Claims, 19 Drawing Sheets

US 8,212,861 B2

MEDICAL APPARATUS

CROSS REFERENCE TO RELATED APPLICATION

This application is a continuation application of PCT/JP2011/058889 filed on Apr. 8, 2011 and claims benefit of Japanese Application No. 2010-188636 filed in Japan on Aug. 25, 2010, the entire contents of which are incorporated herein by this reference.

BACKGROUND OF THE INVENTION

1. Field of the Invention

The present invention relates to a medical apparatus provided with an image pickup apparatus, which is configured to be introduced in a body for observing a region to be examined.

2. Description of the Related Art

As is well known, endoscope apparatuses, which are medical apparatuses, include an image pickup apparatus and are configured to be introduced into a body cavity of a patient to carry out various kinds of examination, treatment and the like of a diseased part in the body based on observed images photographed by the image pickup apparatus.

Endoscopes for medical use include an endoscope of a type configured to be introduced into digestive organs such as esophagus, stomach, large intestine, duodenum, and the like, which are tube cavities in a body, from the oral cavity or the anus, and an endoscope of a type configured to be introduced into an abdominal cavity by puncturing the body wall from near the umbilical region and penetrating through the body wall. Conventional endoscopes have an elongated insertion portion, and the insertion portion is inserted into a digestive tract or an abdominal cavity. In recent years, there have been also known medical apparatuses which include no insertion portion and which are provided with an image pickup apparatus for observing a region to be examined in a body.

For example, Japanese Patent Application Laid-Open Publication No. 2009-72367 discloses a medical apparatus which includes: a medical instrument configured to be fixed to a body wall in a body cavity and including an image pickup section; and a posture control section for moving a posture of the medical instrument from the extracorporeal side. In the conventional medical apparatus, there is disclosed a technology for changing a field of view direction of the image pickup section by changing the posture of the medical instrument fixed to the body wall in a non-contact fashion by a magnetic force of a magnet by operating the posture control section.

Furthermore, for example, Japanese Patent Application Laid-Open Publication No. 2010-12222 discloses a medical apparatus which includes a medical instrument configured to be fixed to a body wall in a body cavity by a fixing section and having an image pickup section. In the conventional medical apparatus, there is disclosed a technology for varying an illumination direction of an illumination section with respect to the field of view direction of the image pickup section of the medical instrument.

SUMMARY OF THE INVENTION

A medical apparatus according to one aspect of the present invention includes: an image pickup apparatus to be introduced in a body and retained therein; a retaining/fixing section configured to contact a body wall in the body, for retaining and fixing the image pickup apparatus at the body wall; a plurality of operation wires configured to be operated from an extracorporeal side; and an observation direction control section for changing an observation direction of the image pickup apparatus by operation of the plurality of wires, wherein the observation direction control section includes: an image pickup apparatus fixing section configured to be connected to the operation wires and to contact an outer surface part of the image pickup apparatus; and a rotary section configured to support the retaining/fixing section and the image pickup apparatus fixing section so as to be separated from each other by a predetermined distance, and allow the image pickup apparatus fixing section to rotate with respect to the retaining/fixing section with a rotation center as a fulcrum, based on the operation of the plurality of operation wires.

A medical apparatus according to another aspect of the present invention includes: an image pickup apparatus to be introduced in a body and retained therein; a retaining/fixing section configured to contact a body wall in the body, for retaining and fixing the image pickup apparatus at the body wall; a plurality of operation wires configured to be operated from an extracorporeal side; and an observation direction control section including a plurality of projectable/retractable protrusion portions respectively connected to the plurality of operation wires, the observation direction control section changing an observation direction of the image pickup apparatus by projecting and retracting the plurality of protrusion portions to bring the protrusion portions into contact with the body wall, by pulling or relaxing operation of the plurality of operation wires.

DETAILED DESCRIPTION OF THE PREFERRED EMBODIMENT(S)

Hereinafter, embodiments of the present invention will be described with reference to drawings. Note that the following description exemplifies a medical apparatus for performing a laparoscopic surgery, for example. In addition, in the description below, each of the drawings according to each of the embodiments is a pattern diagram, and care should be taken to the fact that the relationship between the thicknesses and widths of the respective components, a ratio of the thickness of a certain component to others, and the like are different from the actual sizes. It is needless to say that the relationship and ratio among the dimensions of the components are sometimes different from one drawing to another.

(First Embodiment)

Figure 1:
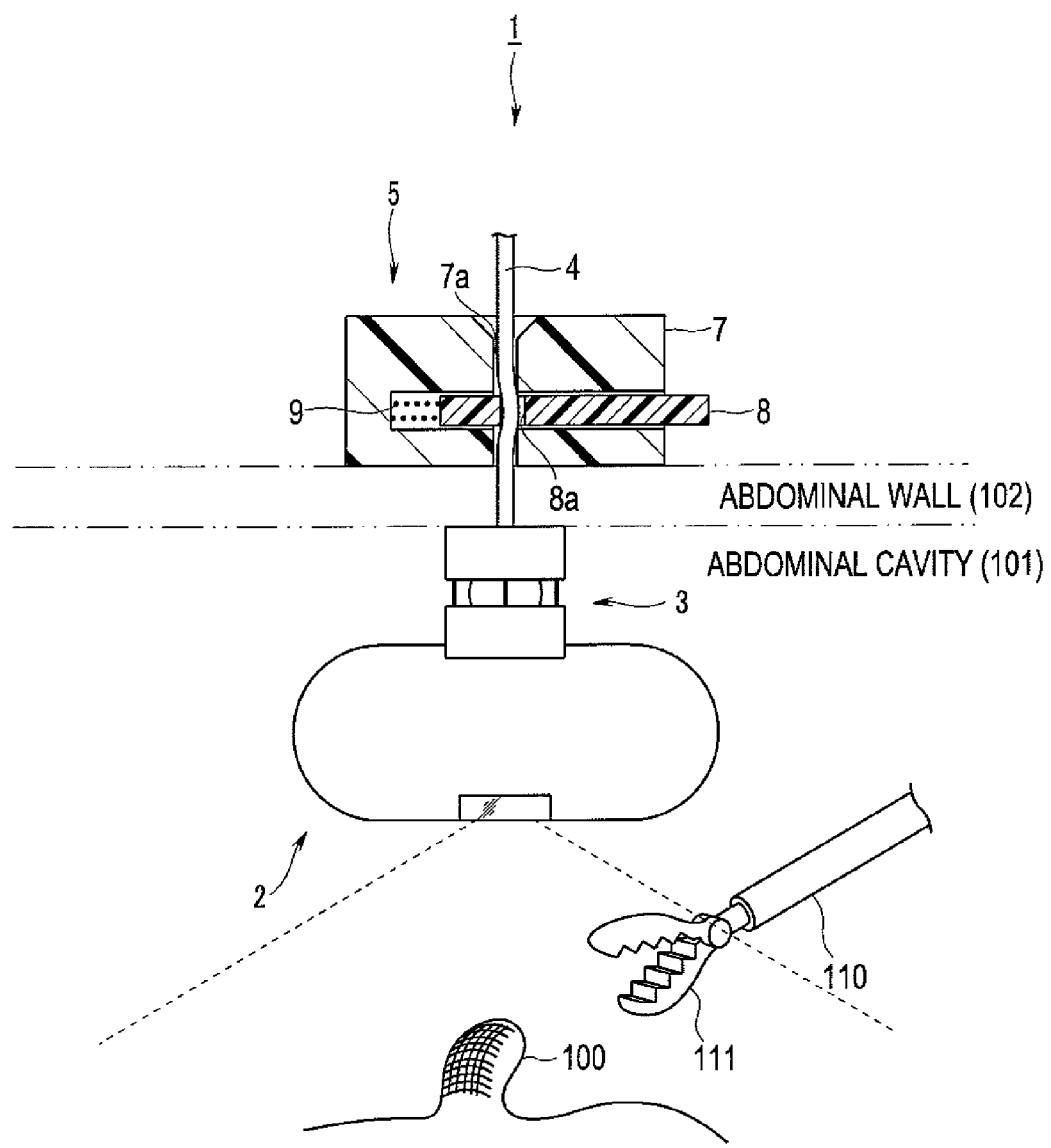
FIG. 1 relates to a first embodiment of the present invention and is a view showing a configuration of an abdominal camera system including an intra-abdominal cavity set camera and a posture control unit that are set in an abdominal cavity.
Figure 2:
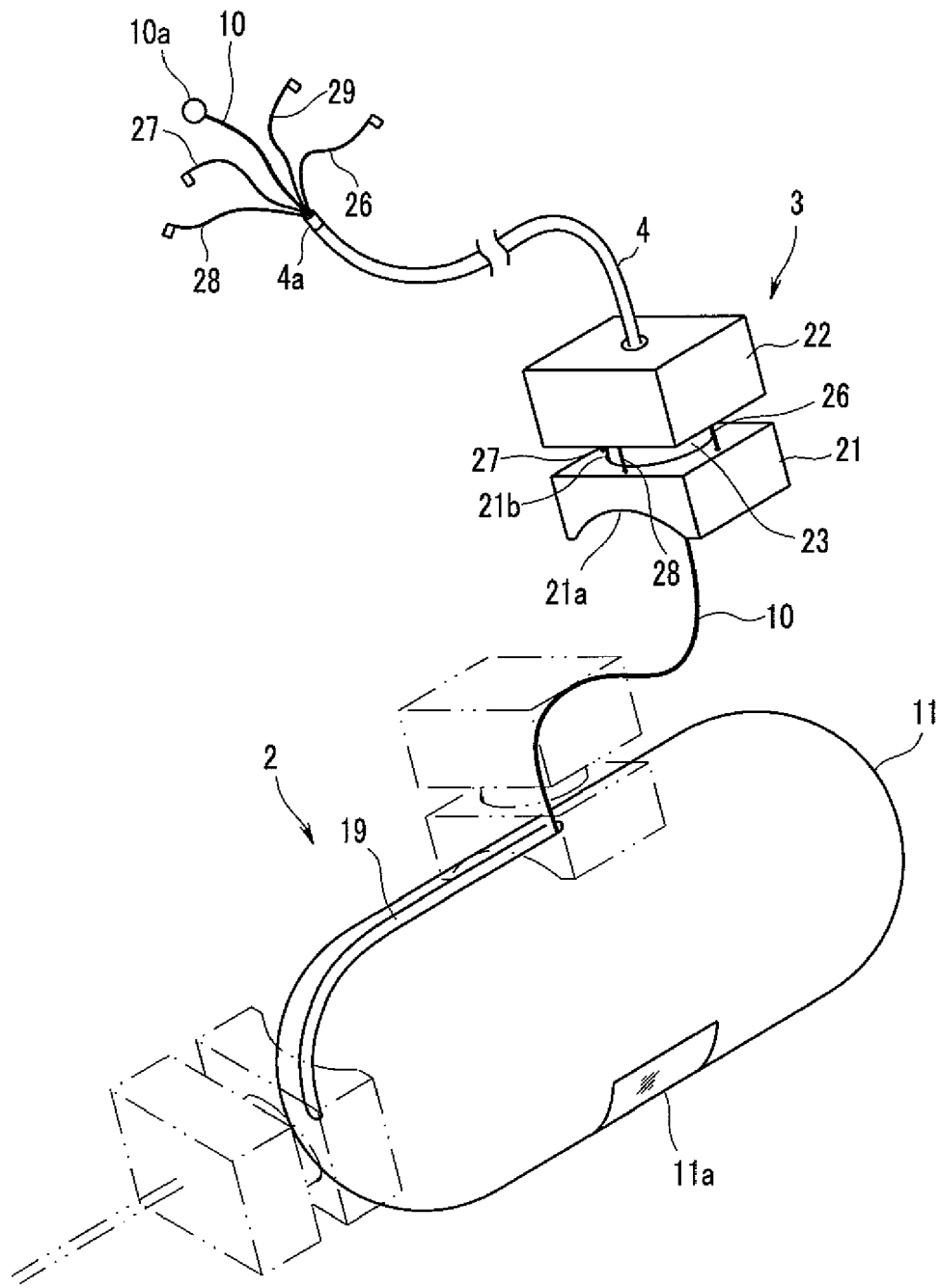
FIG. 2 relates to the first embodiment of the present invention and is a perspective view showing configurations of the intra-abdominal cavity set camera and the posture control unit.
Figure 3:
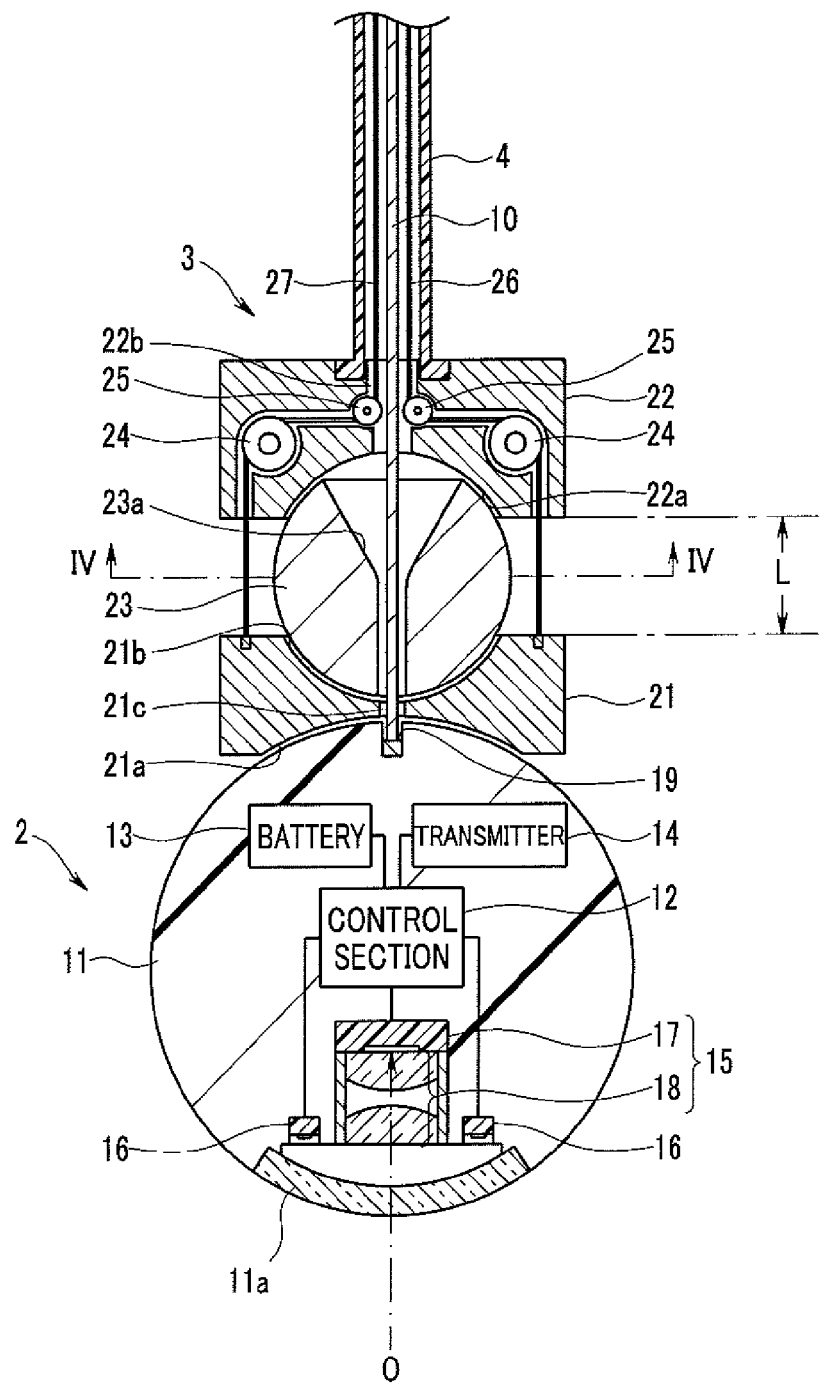
FIG. 3 relates to the first embodiment of the present invention and is a cross-sectional view schematically showing internal configurations of the intra-abdominal cavity set camera and the posture control unit.
Figure 4:
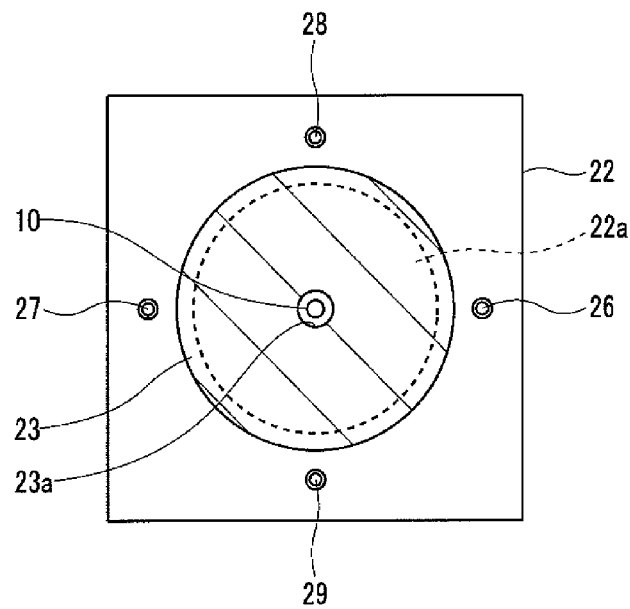
FIG. 4 relates to the first embodiment of the present invention and is a cross-sectional view along the IV-IV line in FIG. 3.
Figure 5:
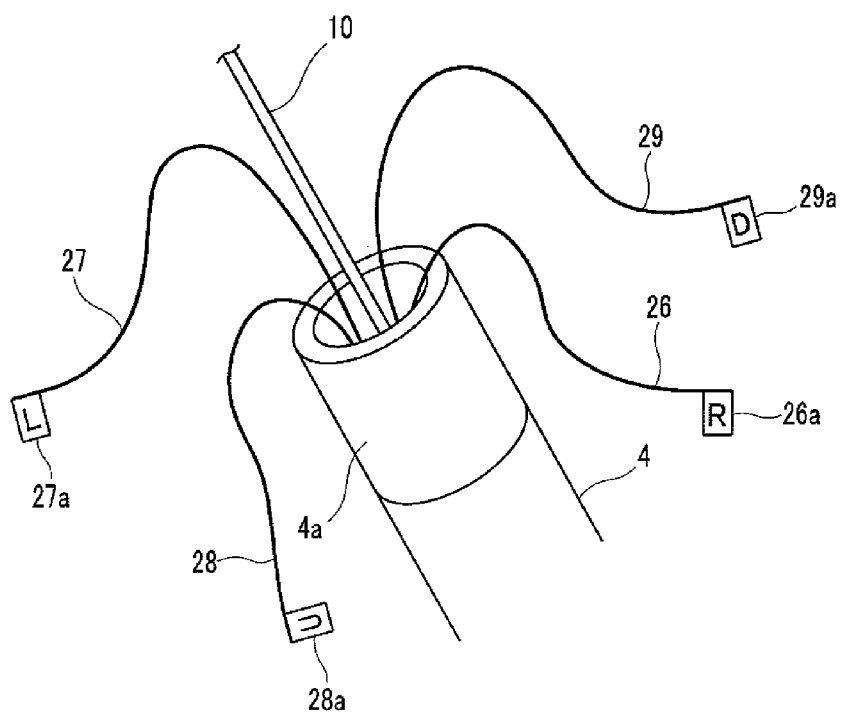
FIG. 5 relates to the first embodiment of the present invention and is a perspective view showing an example in which indicators are provided at end portions of operation wires.
Figure 6:
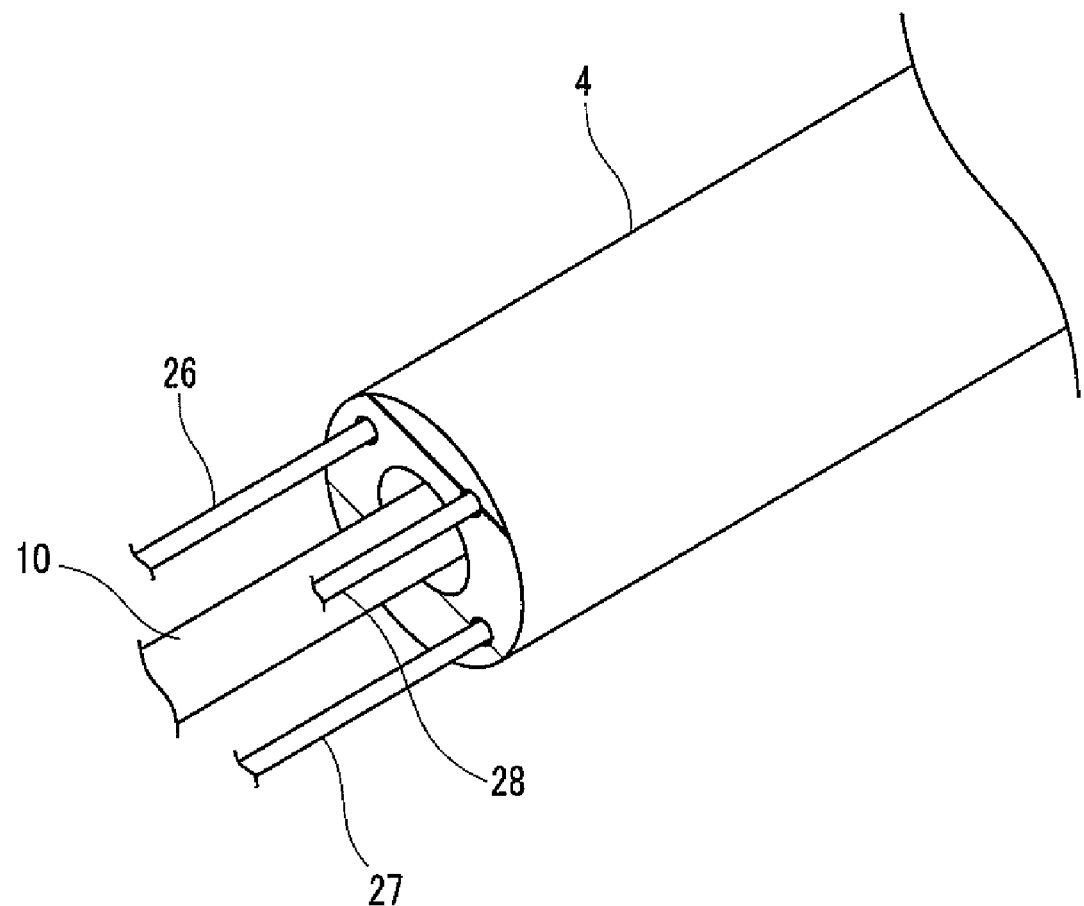
FIG. 6 relates to the first embodiment of the present invention and is a perspective view showing an example in which a hanging tube extended from the posture control unit is configured as a multi-lumen tube.
Figure 7:
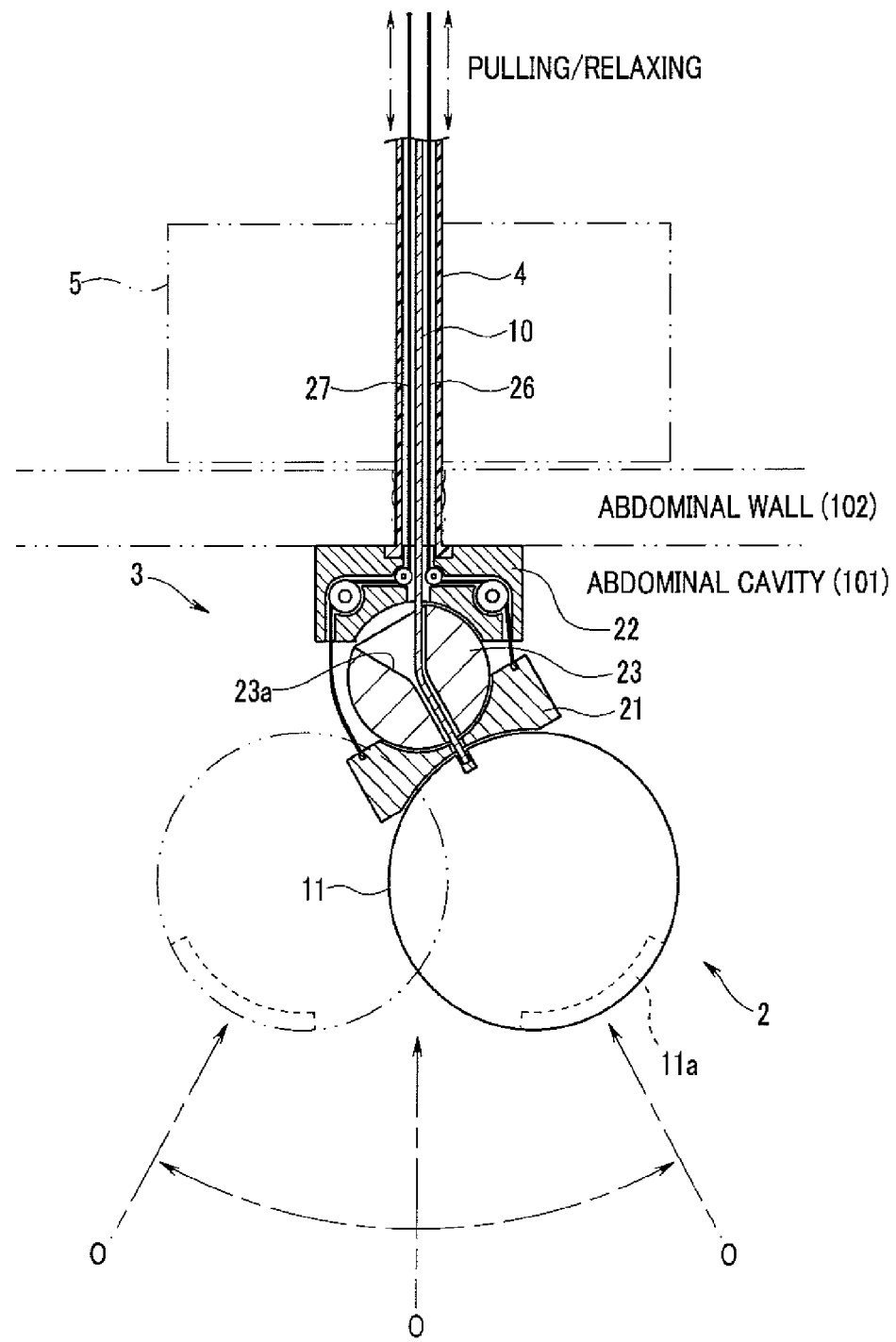
FIG. 7 relates to the first embodiment of the present invention and is a view for illustrating an angle-varying operation of the intra-abdominal cavity set camera fixed to the abdominal wall.
Figure 8:
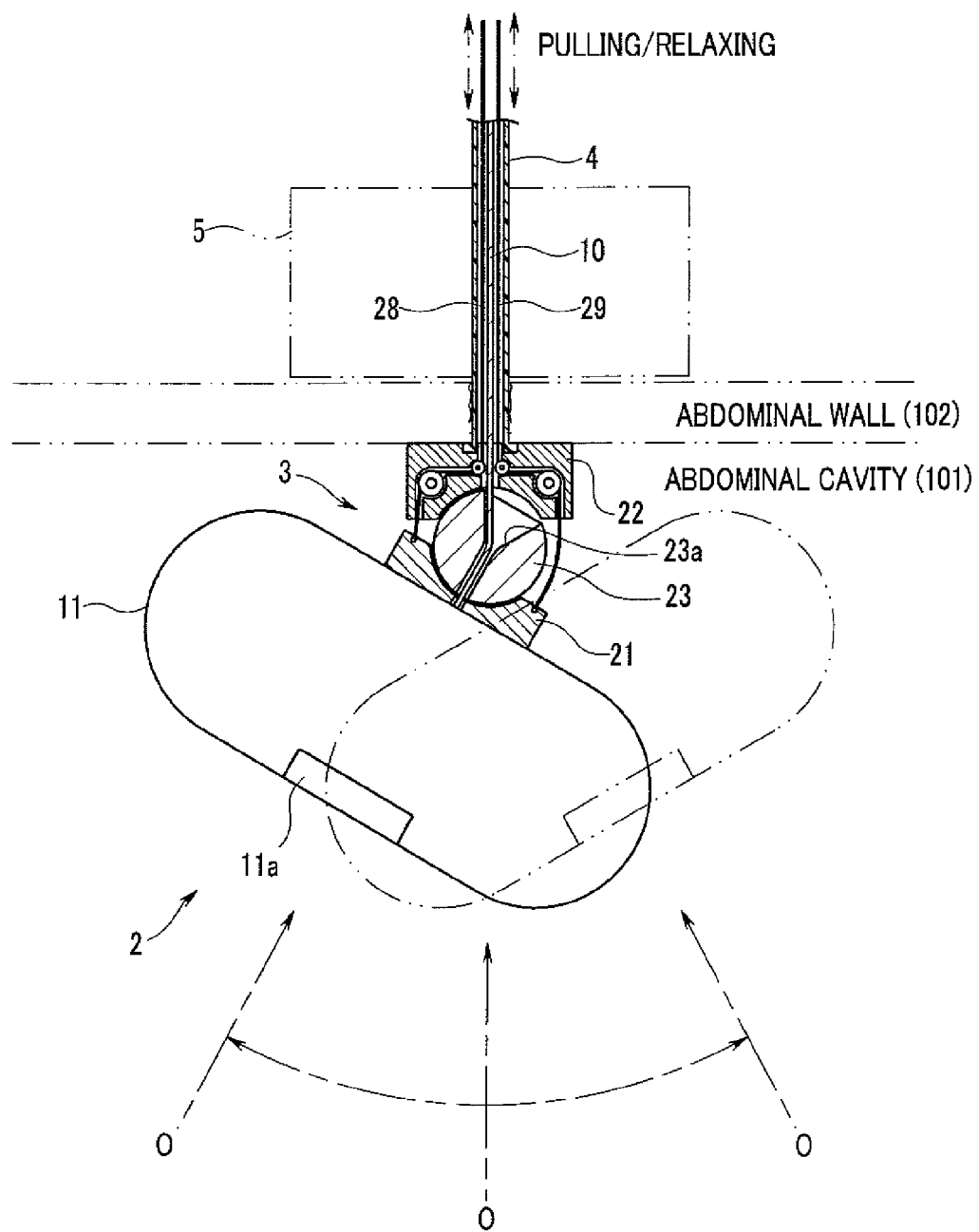
FIG. 8 relates to the first embodiment of the present invention and is a view for illustrating the angle-varying operation of the intra-abdominal cavity set camera fixed to the abdominal wall, when viewed from a direction different from the direction in FIG. 7.
Figure 9:
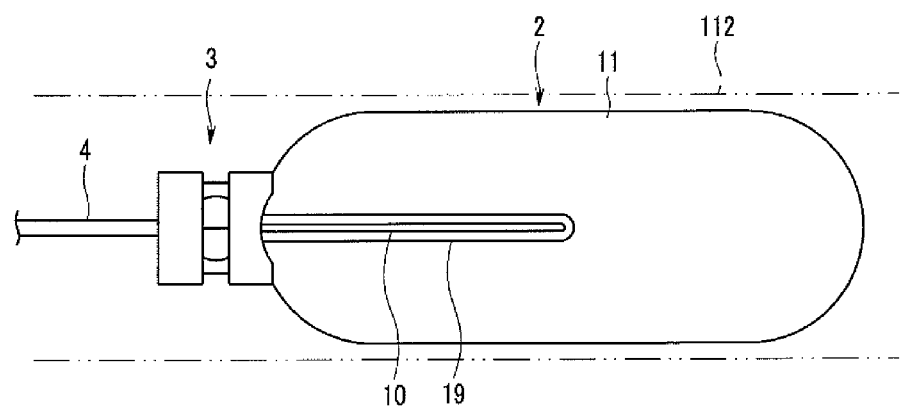
FIG. 9 relates to the first embodiment of the present invention and is a top view of the intra-abdominal cavity set camera and the posture control unit.
Figure 10:
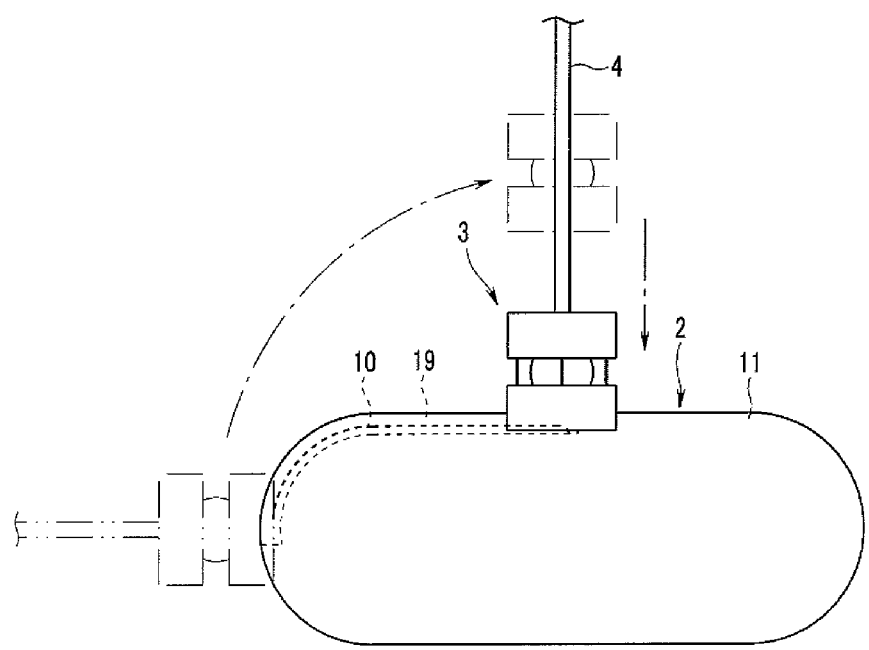
FIG. 10 relates to the first embodiment of the present invention and is a side view of the intra-abdominal cavity set camera and the posture control unit.
Figure 11:
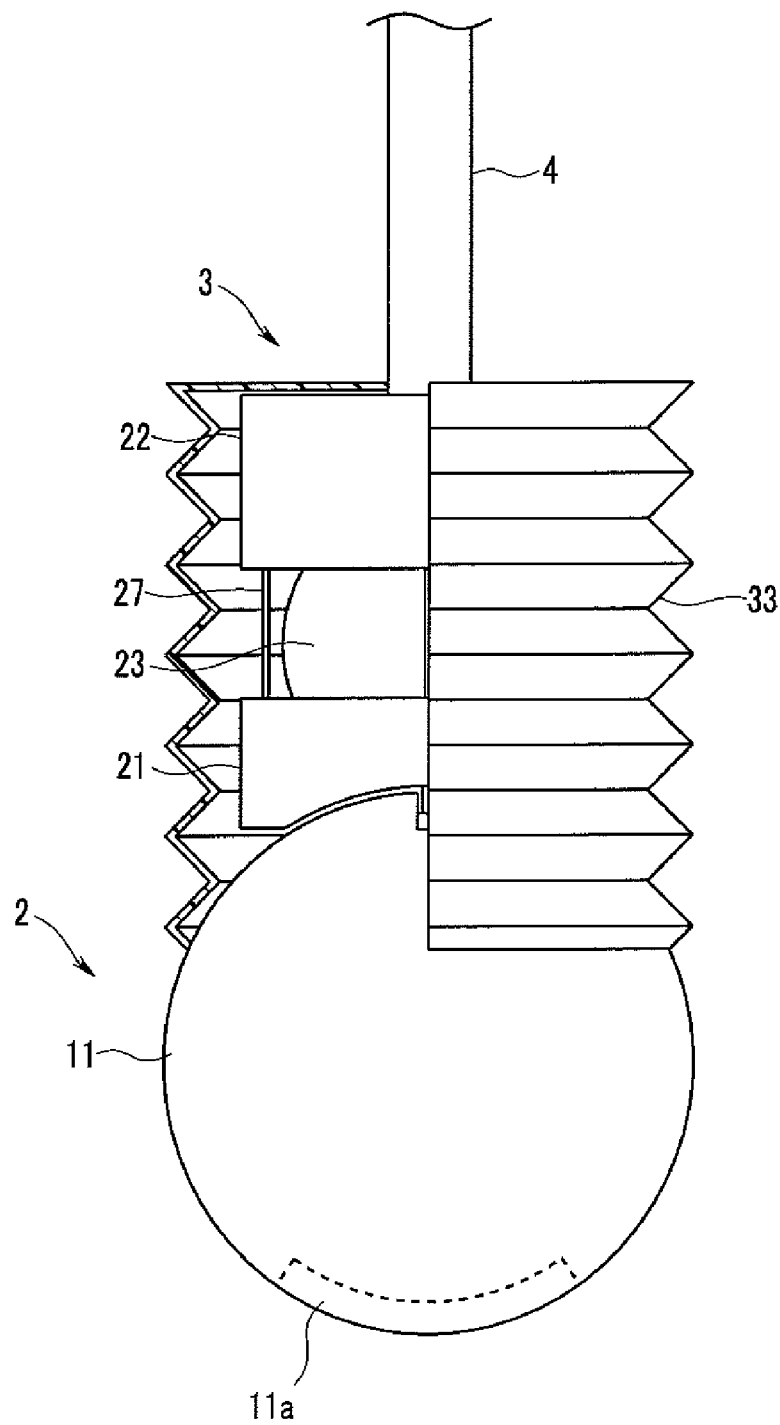
FIG. 11 relates to the first embodiment of the present invention and is a view showing an example of a posture control unit covered with a bellows tube, according to a first modified example.
Figure 12:
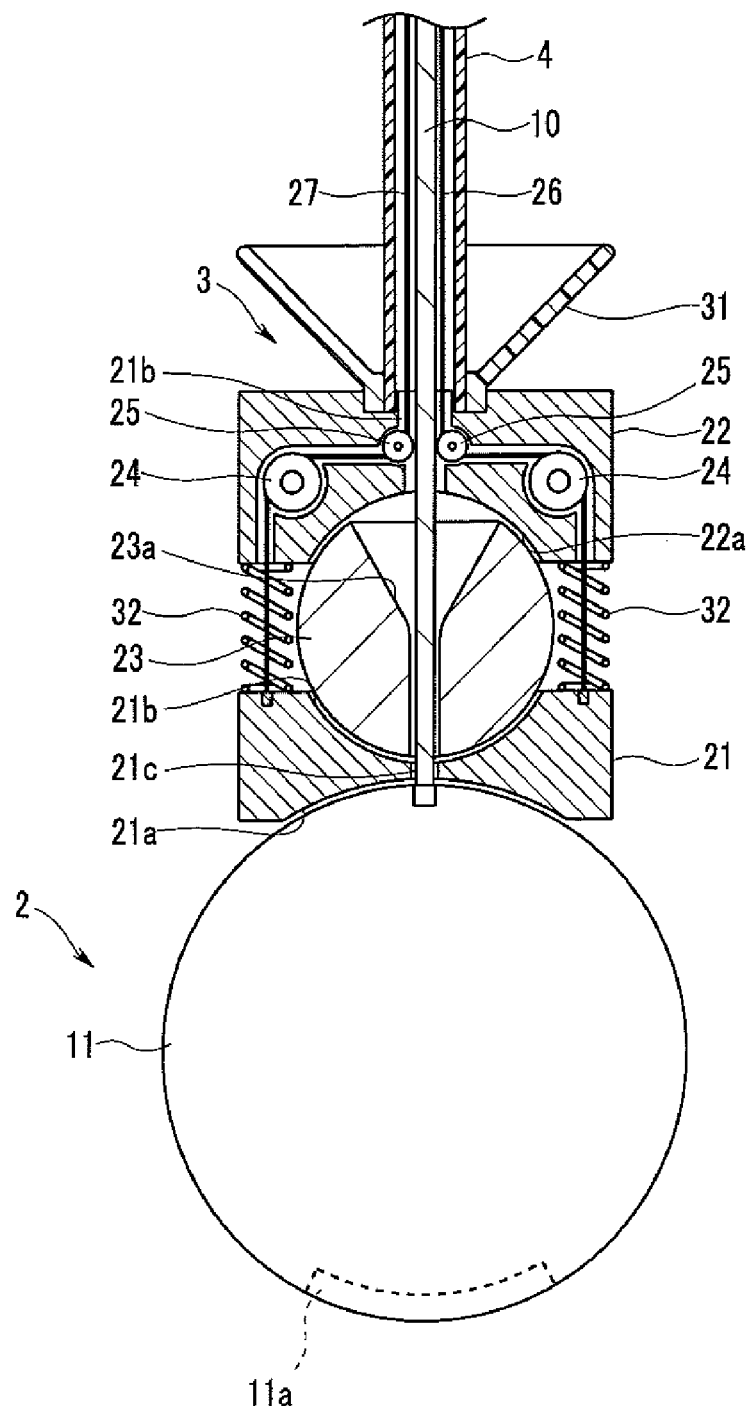
FIG. 12 relates to the first embodiment of the present invention and is a view showing configurations of an intra-abdominal cavity set camera and a posture control unit according to a second modified example.
Figure 13:
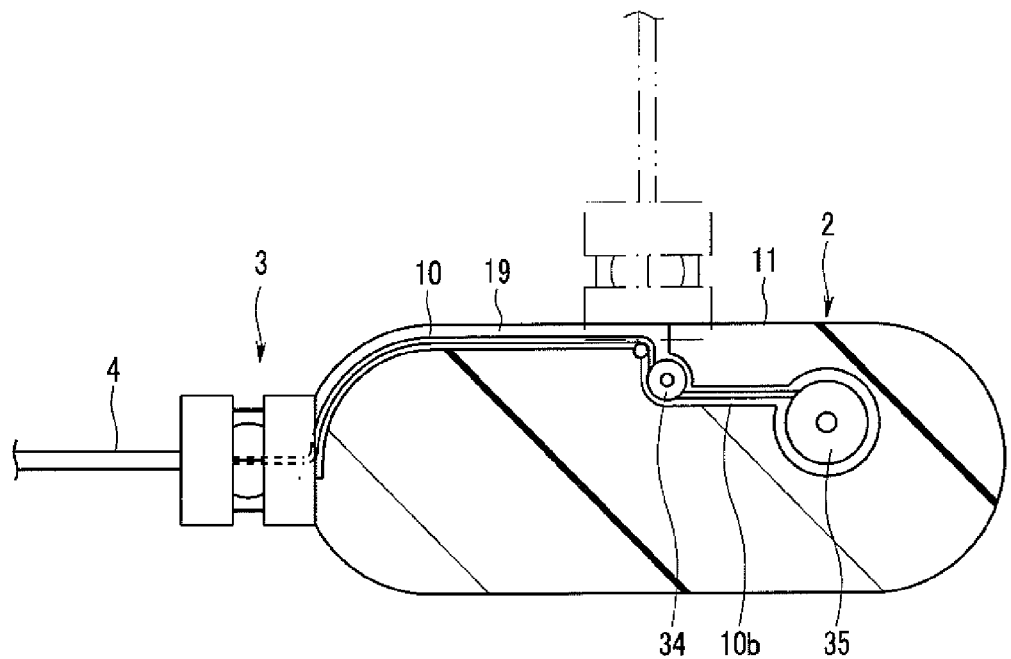
FIG. 13 relates to the first embodiment of the present invention and is a cross-sectional view showing configurations of an intra-abdominal cavity set camera and a posture control unit according to a third modified example.
Figure 14:
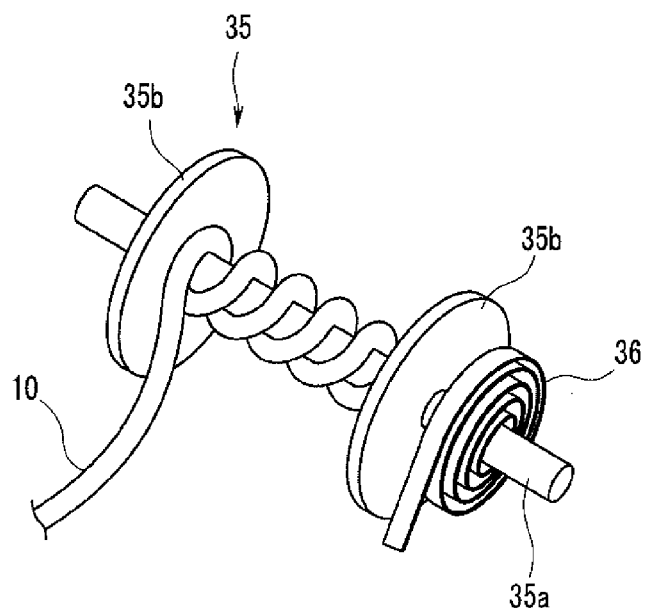
FIG. 14 relates to the first embodiment of the present invention and is a perspective view showing a configuration of a drum around which wires are wound, provided in the intra-abdominal cavity set camera in FIG. 13.
Figure 15:
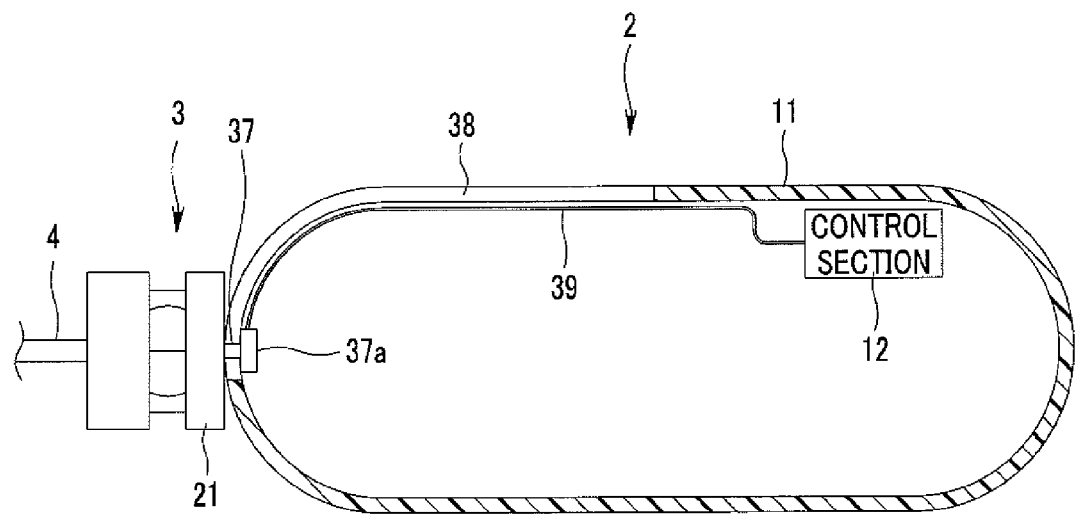
FIG. 15 relates to the first embodiment of the present invention and is a cross-sectional view showing configurations of an intra-abdominal cavity set camera and a posture control unit according to a fourth modified example.
Figure 16:
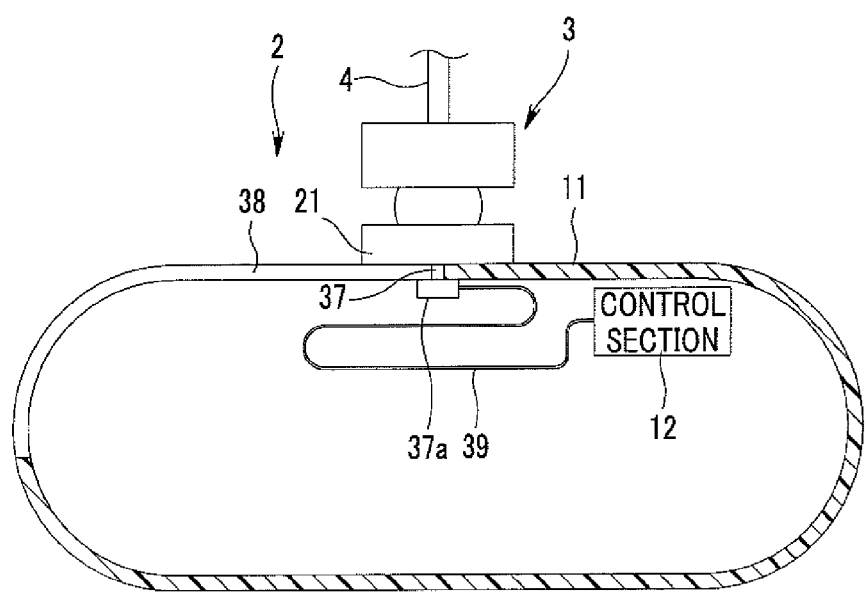
FIG. 16 relates to the first embodiment of the present invention and is a cross-sectional view showing a state where the posture control unit moves to a position different from the position in FIG. 15.

First, description will be made below on an abdominal camera system as a medical apparatus according to the present invention, which is used for a laparoscopic surgery, with reference to FIGS. 1 to 16. Note that FIGS. 1 to 16 relate to the first embodiment of the present invention in which: FIG. 1 is a view showing a configuration of an abdominal camera system including an intra-abdominal cavity set camera and an observation direction control unit that are set in an abdominal cavity; FIG. 2 is a perspective view showing configurations of the intra-abdominal cavity set camera and the observation direction control unit; FIG. 3 is a cross-sectional view schematically showing internal configurations of the intra-abdominal cavity set camera and the observation direction control unit; FIG. 4 is a cross-sectional view along the IV-IV line in FIG. 3; FIG. 5 is a perspective view showing an example in which indicators are provided at end portions of operation wires; FIG. 6 is a perspective view showing an example in which a hanging tube extended from the observation direction control unit is configured as a multi-lumen tube; FIG. 7 is a view for illustrating an angle-varying operation of the intra-abdominal cavity set camera fixed to the abdominal wall; FIG. 8 is a view for illustrating an angle-varying operation of the intra-abdominal cavity set camera fixed to the abdominal wall, when viewed from a direction different from the direction in FIG. 7; FIG. 9 is a top view of the intra-abdominal cavity set camera and the observation direction control unit; FIG. 10 is a side view of the intra-abdominal cavity set camera and the observation direction control unit; FIG. 11 is a view showing an example of an observation direction control unit covered with a bellows tube, according to a first modified example; FIG. 12 is a view showing configurations of an intra-abdominal cavity set camera and an observation direction control unit according to a second modified example; FIG. 13 is a cross-sectional view showing configurations of an intra-abdominal cavity set camera and an observation direction control unit according to a third modified example; FIG. 14 is a perspective view showing a configuration of a drum around which wires are wound, provided in the intra-abdominal cavity set camera in FIG. 13; FIG. 15 is a cross-sectional view showing configurations of an intra-abdominal cavity set camera and an observation direction control unit according to a fourth modified example; and FIG. 16 is a cross-sectional view showing a state where the observation direction control unit moves to a position different from the position in FIG. 15.

As shown in FIGS. 1 and 2, an abdominal camera system (hereinafter, just referred to a camera system in some cases) 1 as a medical apparatus according to the present embodiment is configured by mainly including: an intra-abdominal cavity set camera (hereinafter, just referred to as a camera) 2 as an image pickup apparatus (image pickup means) which is a medical instrument main body having a capsule outer body and including inside thereof an image pickup section; an observation direction control unit 3 as an observation direction control mechanism (observation direction control means) for changing a posture of the camera 2 and controlling an observation direction; a hanging tube 4 as a flexible tube body which is configured to be extended from an upper surface center of the observation direction control unit 3 in the present embodiment; and a fixing unit 5 configuring one of retaining/fixing apparatuses (retaining/fixing means) for retaining and fixing the camera 2 introduced into an abdominal cavity 101 at an abdominal wall 102 which is a body wall by inserting the hanging tube 4 therethrough and fixing the hanging tube 4 on the extracorporeal side.

Note that a wire 10 is extended from the upper center of the camera 2, as shown in FIG. 2. The wire 10 is inserted and arranged in the hanging tube 4 and extracted from an extension end portion of the hanging tube 4. In addition, a stopper member 10a for preventing the wire from being fallen off from the hanging tube 4 is provided at an extension end of the wire 10.

The camera 2 according to the present embodiment is used for a laparoscopic surgery, for photographing a diseased part 100 as a region to be treated when performing treatment on organs in the abdominal cavity 101 as one of body cavities of a patient, by using a treatment instrument, for example, a grasping forceps 110 having at the distal end thereof a grasping portion 111.

First, the camera 2 is introduced into the abdominal cavity 101 as a body cavity in the body of the patient through a trocar, not shown here, which is punctured into the abdominal wall 102 and serves as an introduction port into the abdominal cavity 101. Then, the camera 2 is hooked by hooking the hanging tube 4 with a puncture needle, not shown here, which is punctured in the abdominal cavity 101, and the hanging tube 4 is pulled outside the body so as to penetrate the abdominal wall 102.

Next, the hanging tube 4 is inserted in a hole portion 7a formed so as to penetrate a housing 7 in a vertical direction from a center of the housing 7 of the fixing unit 5 prepared on the abdominal side of the patient, and pulled toward the abdominal wall 102 as a body cavity wall. Note that the hanging tube 4 has, at the extension end thereof, a rigid cap tube 4a (see FIG. 2 and FIG. 5) made of metal and the like.

Then, the camera 2 and the observation direction control unit 3 are lifted so as to get close to the abdominal wall 102 by the hanging tube 4 and the wire 10 inserted through the hanging tube 4 being pulled toward the extracorporeal side so as to be away from the patient. At this time, the hanging tube 4 and the wire 10 are pulled toward the extracorporeal side until the upper surface of the observation direction control unit 3 abuts the inner wall surface of the abdominal wall 102. Thus, the camera 2 is retained and fixed at the abdominal wall 102 in the abdominal cavity 101 through the observation direction control unit 3, in a state hauled up by the wire 10 inserted through the hanging tube 4.

Note that the fixing unit 5, which is set on the abdominal wall 102 on the extracorporeal side of the patient, is provided with a fixing lever 8 which fixes the hanging tube 4 of the camera 2 on the extracorporeal side. At the halfway portion of the fixing lever 8, a hole portion 8a through which the hanging tube 4 is inserted and penetrated is formed. The hole portion 8a is biased to one side direction of the housing 7 by a spring 9 provided in the housing 7 such that the position of the hole portion 8a is displaced from the position of the hole portion 7a formed in the housing 7 of the fixing unit 5.

That is, a user pushes the fixing lever 8 into the housing 7 against the biasing force of the spring 9 until the hole portion 8a of the fixing lever 8 reaches a position coincident with the position of the hole portion 7a of the housing 7, thereby easily enabling the hanging tube 4 to move relatively (move slidingly) with respect to the housing 7 of the fixing unit 5.

When the user releases pushing of the fixing lever 8 into the housing 7, the fixing lever 8 is subjected to the biasing force of the spring 9 to slide in one side direction which is the inner direction of the housing 7. As a result, the position of the hole portion 8a of the fixing lever 8 is displaced with respect to the position of the hole portion 7a of the housing 7, thereby allowing the hanging tube 4 inserted through the hole portions 7a, 8a, to be held and fixed in the housing 7 of the fixing unit 5.

The upper surface of the observation direction control unit 3 abuts the inner wall surface on the intracorporeal side of the abdominal wall 102 in a surface-contact manner in the abdominal cavity 101, and the camera 2 is hauled up by the wire 10 in the hanging tube 4. The camera 2 is thus retained and fixed in the abdominal cavity 101 in a stable state.

Next, a specific configuration of the camera 2 will be detailed with reference to FIGS. 2 and 3.

As shown in FIGS. 2 and 3, the camera 2 according to the present embodiment incorporates, in a main body section 11 as an external housing, a control section 12 as control means, a battery 13 as a power supply (power supplying means) which supplies power to the control section 12, a transmitter 14 which is electrically connected to the control section 12, an image pickup unit 15 as image pickup means which is an image pickup section electrically connected to the control section 12, and a plurality of illumination sections 16 which are disposed on both sides of the image pickup unit 15 and electrically connected to the control section 12, and which are illumination means having LED light sources in the present embodiment.

The image pickup unit 15 includes a solid-state image pickup device 17 which is a CCD or a CMOS mounted on a processing substrate, and an objective lens group 18 arranged on a subject side (photographing object point side) which is a forward of the solid-state image pickup device 17. In addition, the image pickup unit 15 photographs inside of the abdominal cavity 101 through a cover glass 11a as an observation window arranged on the main body section 11. The cover glass 11a is disposed on the main body section 11 at a position which is opposite side of the wire 10 extended from the center of the upper portion as defined here, that is, disposed at the center of the lower portion of the main body section 11.

Note that the transmitter 14 wirelessly transmits and outputs an image signal photoelectrically converted by the image pickup unit 15 to a video processor, not shown, as an extracorporeal device. In addition, the image signal transmitted to the video processor is subjected to image processing, and thereafter outputted on a monitor connected to the video processor, thereby allowing an endoscopic image photographed by the camera 2 to be displayed on the monitor (both of the video processor and the monitor are not shown).

Note that a recess-shaped long groove 19 (see FIG. 2) is formed on the outer surface of the main body section 11 of the camera 2, from the upper center to the center of the one side portion. One end of the wire 10 is connected to the end portion of the long groove 19 at the upper center of the main body section 11 of the camera 2. The long groove 19 is formed so as to house the wire 10 inside thereof when the observation direction control unit 3 is moved to one side portion of the camera 2. The function of the configuration of the long groove 19 will be detailed later.

Next, a specific configuration of the observation direction control unit 3 is detailed here with reference to FIGS. 2 and 3 again here.

As shown in FIGS. 2 and 3, the observation direction control unit 3 according to the present embodiment includes substantially rectangular-shaped two block bodies and a substantially spherical-shaped member interposed between the two block bodies.

For details, the observation direction control unit 3 is configured by mainly including: a camera fixing section 21, as one of the two block bodies, which is positioned on the side of the camera 2 located on the lower side (the lower side when viewed facing the paper surface of the drawings); an abdominal wall fixing section 22 as the other of the two block bodies, the upper surface (upper side when viewed facing the paper surface of the drawings) of which is connected with the one end of the hanging tube 4; and a rotary section 23 interposed between the fixing sections 21 and 22 so that the fixing sections 21 and 22 are separated from each other by a predetermined distance.

The camera fixing section 21 which is made of a rigid metal material, for example, includes: an arc surface 21a formed on the lower surface of the fixing section 21 in this case, which is the side of the camera 2, so as to substantially coincide with the outer shape of the main body section 11 of the camera 2; a spherical recessed portion 21b in a spherical crown shape which is formed on the upper surface of the fixing section 21 in this case, which is the side of the rotary section 23, so as to substantially coincide with the spherical surface on the outer surface of the rotary section 23; and a hole portion 21c, through which the wire 10 extended from the camera 2 is inserted and arranged, formed in the vertical direction at the substantially center position of the fixing section 21.

In addition, end portions of four operation wires 26 to 29 are connected and fixed onto the upper surface of the camera fixing section 21. The end portions of the four operation wires 26 to 29 are connected and fixed at positions which are away toward the more peripheral side than the spherical recessed portion 21b and which are substantially equally spaced around the center of the camera fixing section 21.

Note that, as shown in FIG. 1, when the wire 10 is pulled in a state where the upper surface of the abdominal wall fixing section 22 abuts the abdominal wall 102 in a surface-contact manner, the arc surface 21a surface-contacts the outer surface part of the upper center of the main body section 11 of the camera 2 and abuts to be engaged with the main body section 11, thereby allowing the camera fixing section 21 to hold the camera 2 which is being hauled up by the tensional force of the wire 10 in a predetermined direction.

The abdominal wall fixing section 22 is also made of a rigid metal material, for example, and includes on the lower surface thereof in this case, which is the side of the rotary section 23, a spherical recessed portion 22a in a spherical crown shape formed so as to substantially coincide with the spherical surface of the outer surface of the rotary section 23, and a hole portion 22b which communicates with the hanging tube 4. The hole portion 22b of the abdominal wall fixing section 22 is formed so as to penetrate the abdominal wall fixing section 22 in the vertical direction at the substantially center position of the abdominal wall fixing section 22, and the wire 10 extended from the camera 2 is inserted and arranged in the hole portion 22b. The hole portion 22b branches from a halfway portion on the upper side into four directions substantially equally spaced from each other around the center, to communicate with four wire insertion paths through which the operation wires 26 to 29 are inserted, respectively.

The branched four wire insertion paths open at positions which are away toward the more peripheral side than the spherical recessed portion 22a and which are substantially equally spaced around the center of the abdominal wall fixing section 22, as shown in FIG. 4, and extend in the horizontal direction so as to communicate with the hole portion 22b and formed in an L-shape extending downward inside of the abdominal wall fixing section 22, as shown in FIG. 3. In addition, pulleys 24 and 25 for reducing sliding resistance of each of the operation wires 26 to 29 in the wire insertion paths are provided at each of the corner portions and each of the opening parts on the side of the hole portion 22b of the four wire insertion paths in the abdominal wall fixing section 22.

The rotary section 23 is also made of rigid metal material, for example, and has at the center thereof an wire insertion hole portion 23a through which the wire 10 is inserted and arranged. The wire insertion hole portion 23a is formed in a tapered conical shape from the side of the abdominal wall fixing section 22 which is defined as the upper side in this case to the halfway portion toward the side of the camera fixing section 21 which is defined as the lower side in this case.

As shown in FIG. 1, in the sate where the upper surface of the abdominal wall fixing section 22 abuts the abdominal wall 102 in a surface-contact manner, if the wire 10 is pulled and the camera 2 is hauled up, the lower outer surface of the substantially spherical rotary section 23 surface-contacts the spherical recessed portion 21b of the camera fixing section 21, and the upper outer surface of the rotary section 23 surface-contacts the spherical recessed portion 22a of the abdominal wall fixing section 22. At this time, the camera fixing section 21 and the abdominal wall fixing section 22 are apart from each other by a predetermined clearance L in the state where the surfaces opposing to each other, that is, the upper surface of the camera fixing section 21 and the lower surface of the abdominal wall fixing section 22 are in parallel with each other (see FIG. 3).

That is, in the state where the upper surface of the abdominal wall fixing section 22 abuts the abdominal wall 102 in a surface-contact manner as shown in FIG. 1, the observation direction control unit 3 enables the abdominal wall fixing section 22 to be inclined with respect to the camera fixing section 21, with the center of the rotary section 23 as a fulcrum.

When the observation direction control unit 3 thus configured is retained and fixed at the abdominal wall 102 in the abdominal cavity 101, the observation direction control unit 3 is configured to enable the camera fixing section 21 to be rotatable, with the center of the rotary section 23 as a fulcrum, within a range abutting the abdominal wall fixing section 22. The rotation operation of the camera fixing section 21 with respect to the abdominal wall fixing section 22 is performed by pulling or relaxing the above-described four operation wires 26 to 29.

According to such a configuration, in the state where the observation direction control unit 3 is retained and fixed at the abdominal wall 102 in the abdominal cavity 101, the outer surface part of the upper center of the main body section 11 of the camera 2 is engaged with the arc surface 21a of the camera fixing section 21 to be held thereat, which allows the posture of the camera 2 to be inclined in conjunction with the camera fixing section 21 which is inclined by pulling or relaxing operation of the four operation wires 26 to 29. Therefore, the observation direction (see the photographing optical axis O in FIG. 7) of the photographing light incident on the image pickup unit 15 of the camera 2 is changed. That is, the photographing direction of the camera 2 retained and fixed in the body is changed by performing pulling or relaxing operation of the four operation wires 26 to 29 from the extracorporeal side.

Note that the respective four operation wires 26 to 29 are inserted and arranged in the hanging tube 4 and extended from the end portion of the hanging tube 4 (see FIG. 2). Furthermore, the respective extension ends of the operation wires 26 to 29 are provided with indicator portions 26a to 29a which also serve as portions for preventing the wires from falling off from the hanging tube 4, as shown in FIG. 5. It is preferable that the indicator portions 26a to 29a are configured such that the operation direction, i.e., up (U . . . UP), down (D... DOWN), right (R... RIGHT) or left (L... LEFT) direction, which corresponds to the direction in which the camera fixing section 21 is rotated in accordance with the up, down, right, or left of the image photographed by the image pickup unit 15 of the camera 2 can be easily recognized, for example, when each of the operation wires 26 to 29 to which each of the indicator portions 26a to 29a is attached is pulled individually.

Furthermore, as shown in FIG. 6, the hanging tube 4 is configured as a multi-lumen tube including a plurality of, e.g., five wire insertion paths in the present embodiment through which the wire 10 and the four operations wires 26 to 29 are respectively inserted, thereby preventing the wire 10 and the four operation wires 26 to 29 from being entangled.

In the camera system 1 configured as described above according to the present embodiment, as shown in FIGS. 7 and 8, the observation direction (direction of the photographing optical axis O) is changed by pulling or relaxing the four operation wires 26 to 29 individually or plural wires among the four operation wires at the same time from the extracorporeal side in the state where the camera 2 is retained and fixed at the abdominal wall 102 in the abdominal cavity 101 through the observation direction control unit 3.

That is, in the camera system 1, by performing pulling or relaxing operation of the four operation wires 26 to 29, the posture angle in the lateral direction of the main body section 11 of the camera 2 as shown in FIG. 7 and the posture angle in the longitudinal direction of the main body section 11 of the camera 2 as shown in FIG. 8 are changed in the state where the camera 2 is retained and fixed at the abdominal wall 102 in the abdominal cavity 101 through the observation direction control unit 3, that is, the inclination of the main body section 11 of the camera 2 is changed with the center of the rotary section 23 as a fulcrum, thereby enabling the observation (field of view) direction of the image pickup unit 15 of the camera 2 to be easily changed in a direction desired by a user.

In addition, the camera system 1 enables the camera fixing section 21 of the observation direction control unit 3 to be quickly responsive and incline based on the pulling or relaxing operation of the four wires 26 to 29, thereby providing also an advantage that the operation response performance is excellent at the time of varying the observation (field of view) direction of the image pickup unit 15 of the camera 2.

As described above, the camera system 1 according to the present embodiment is capable of easily changing the observation (field of view) direction of the camera 2 set in the abdominal cavity 101 inside the body in a direction desired by a user, based on the operation of the four operation wires 26 to 29 from the extracorporeal side, and has an excellent response performance of changing the observation (field of view) based on the operation.

Incidentally, as described above, the camera 2 has the recess-shaped long groove 19 (see FIG. 2) formed on the outer surface of the main body section 11 from the upper center to the center of the one side portion in the present embodiment. As shown in FIG. 9, the long groove 19 can house inside thereof the wire 10 extended from the camera 2 along the recessed shape, when the observation direction control unit 3 is moved to the one side portion of the camera 2.

Thus, by moving the observation direction control unit 3 to the one side portion of the camera 2, the camera 2 and the observation direction control unit 3 are easily inserted into a trocar 112 as an introduction port into the abdominal cavity 101, when the camera 2 and the observation direction control unit 3 are introduced in the abdominal cavity 101 from the extracorporeal side. According to such a configuration, the camera 2 and the observation direction control unit 3 are not get hung up on the trocar 112, thereby improving the introducibility into the trocar 112. As a result, the camera 2 and the observation direction control unit 3 can be smoothly introduced into the abdominal cavity 101.

Note that, after introducing the camera 2 and the observation direction control unit 3 into the abdominal cavity 101 through the trocar 112, as shown in FIG. 10, the wire 10 is hauled up toward the extracorporeal side, and the observation direction control unit 3 is slid to the camera 2 side along the wire 10 together with the hanging tube 4.

FIRST MODIFIED EXAMPLE

As shown in FIG. 11, a stretchable/contractable bellows tube (accordion tube) 33 for covering the observation direction control unit 3 may be provided. Note that the observation direction control unit 3 may be covered with a flexible rubber boot, for example, without limiting to the bellows tube 33.

SECOND MODIFIED EXAMPLE

As shown in FIG. 12, a suction cup 31 may be provided, for sucking and fixing the abdominal wall 102 on the abdominal wall fixing section 22 of the observation direction control unit 3. The suction cup 31 enables the observation direction control unit 3 and the camera 2 to be stably retained at the abdominal wall 102.

In addition, a spring 32 may be provided between the camera fixing section 21 and the abdominal wall fixing section 22. By disposing the spring 32 at four positions so that the operation wires 26 to 29 between the camera fixing section 21 and the abdominal wall fixing section 22 are inserted, respectively, the biasing force of the springs 32 enables the camera fixing section 21 and the abdominal wall fixing section 22 to return to a position at which the separate distance between the opposing surfaces of the camera fixing section 21 and the abdominal wall fixing section 22 is equal to the parallel clearance L (see FIG. 3) in the initial state, without performing the pulling or relaxing operation of the operation wires 26 to 29. Furthermore, the end portion of each of the springs 32 may be secured to the camera fixing section 21 or the abdominal wall fixing section 22 to which the end portion abuts.

THIRD MODIFIED EXAMPLE

As shown in FIG. 13, a drum 35 around which the wire 10 is wound may be provided in the main body section 11 of the camera 2. As shown in FIG. 14, the drum 35 includes a flat spiral spring 36 around a drum shaft 35a, and is biased by the flat spiral spring 36 in the rotation direction in which the wire 10 is wound around the drum shaft 35a between flanges 35b.

Note that, inside the main body section 11, a wire insertion path 10b through which the wire 10 is inserted is formed to a position where the drum 35 is provided, and a pulley 34 for reducing the sliding resistance of the wire 10 is provided at the corner portion of the wire insertion path 10b.

The biasing force of the flat spiral spring 36 thus causes a force to act such that the wire 10 is pulled in the direction wound around the drum 35. Therefore, the laxity of the wire 10 is prevented both in the state where the observation direction control unit 3 is moved to one side portion of the camera 2 and in the state where the camera 2 is retained and fixed at the abdominal wall 102 through the observation direction control unit 3.

FOURTH MODIFIED EXAMPLE

The camera 2 is configured to wirelessly transmitting the signal of the image photographed by the image pickup unit 15. However, the camera 2 may transmit and receive a signal by wired communication by replacing the wire 10 with a communication cable.

In such a configuration, as shown in FIG. 15 and FIG. 16, the observation direction control unit 3 is configured to move along the outer surface of the camera 2 without being separated from the camera 2, thereby capable of reducing the load on a communication cable 39.

Specifically, the observation control unit 3 is configured to move along the outer surface of the camera 2 by connecting a shaft body 37 having a flange 37a hung on the peripheral part (inner surface portion) of the groove 38 in the main body section 11 to the camera fixing section 21 such that the observation direction control unit 3 is movable along the groove 38 formed on the main body section 11 of the camera 2.

Note that the communication cable 39 provided instead of the wire 10 is not limited to the one described above, and may be configured by a flexible printed circuit board (FPC), for example, only inside of the main body section 11 of the camera 2.

(Second Embodiment)

Figure 17:
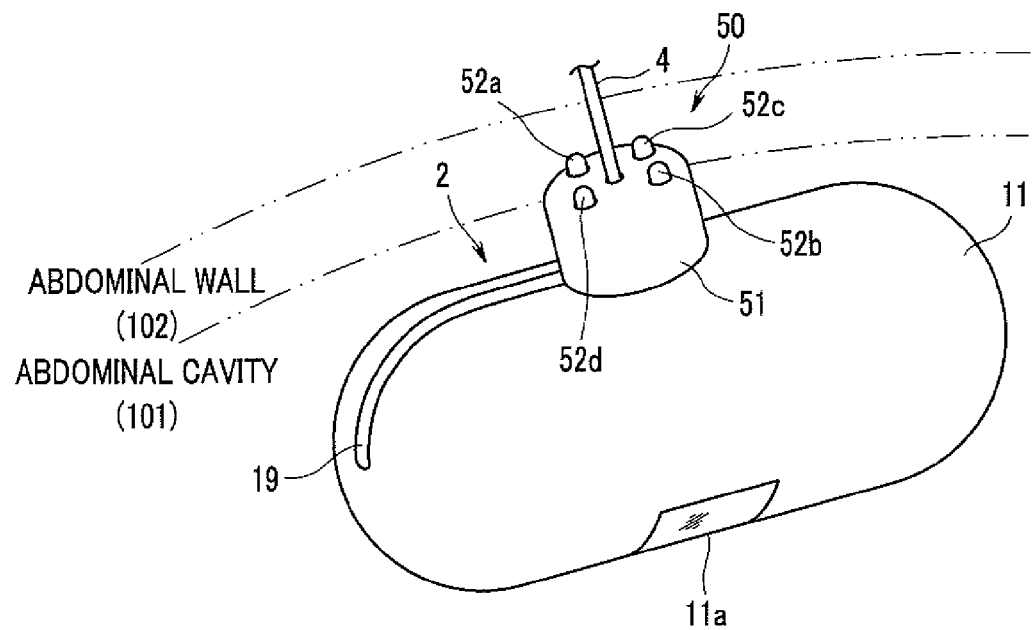
FIG. 17 relates to a second embodiment of the present invention and is a perspective view showing configurations of an intra-abdominal cavity set camera and a posture control unit that are set in the abdominal cavity.
Figure 18:
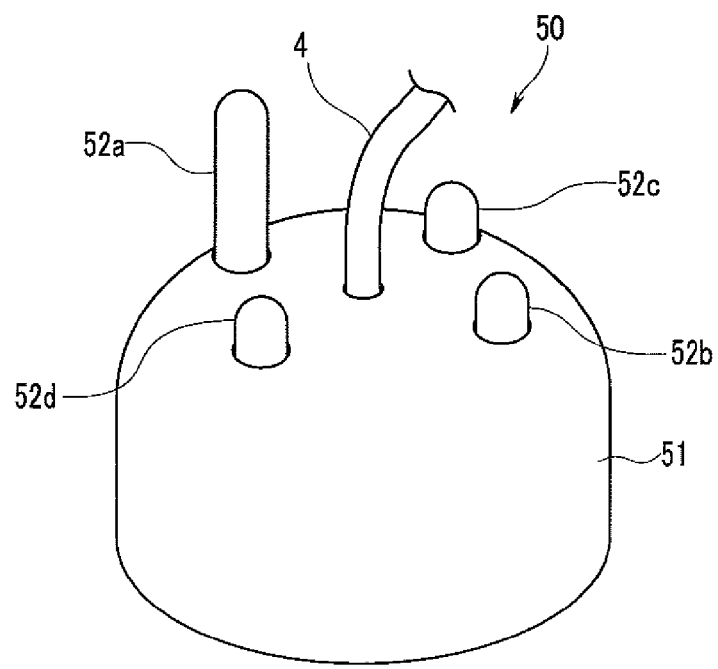
FIG. 18 relates to the second embodiment of the present invention and is a perspective view showing the configuration of the posture control unit.
Figure 19:
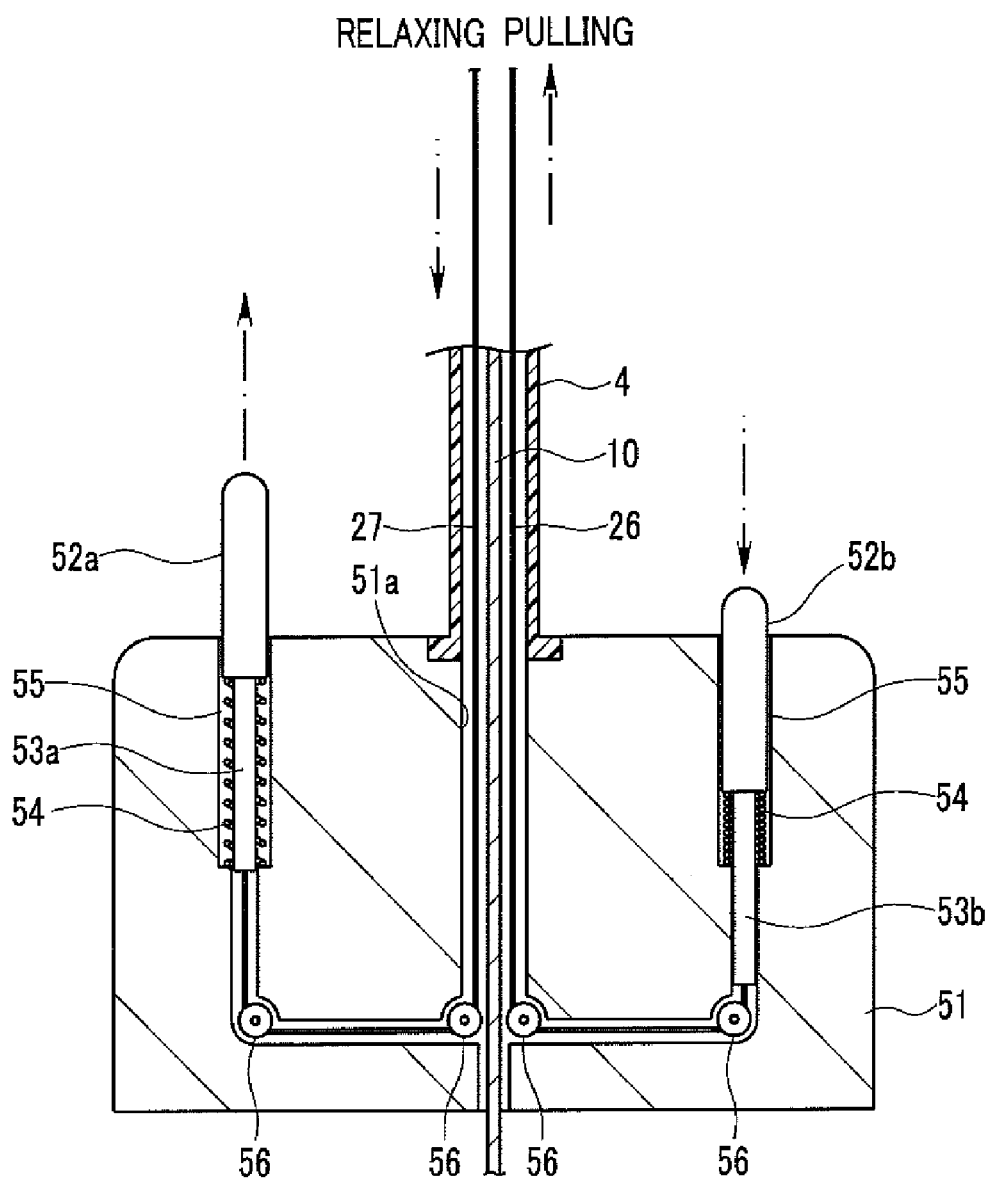
FIG. 19 relates to the second embodiment of the present invention and is a cross-sectional view showing the configuration of the posture control unit.
Figure 20:
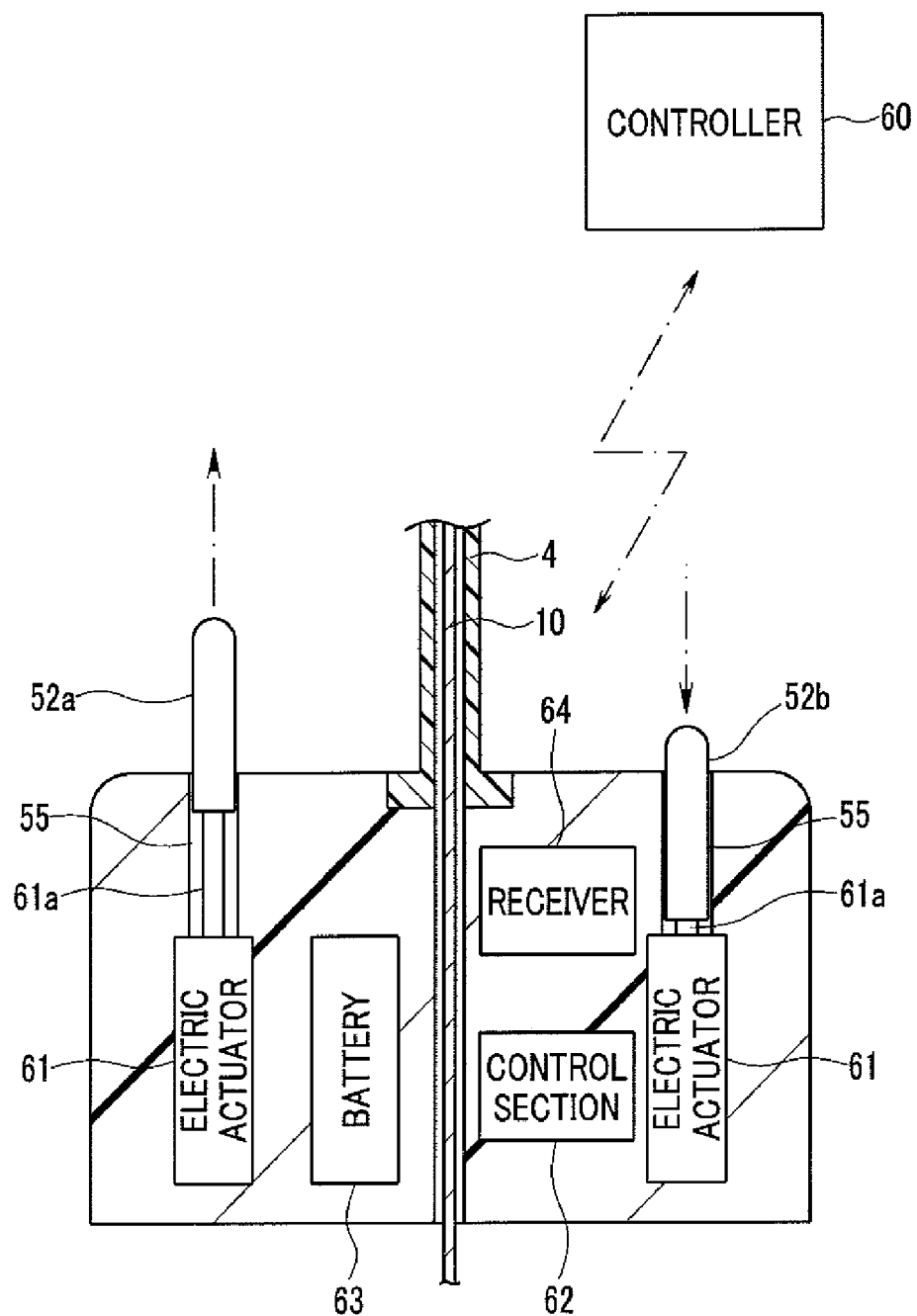
FIG. 20 relates to the second embodiment of the present invention and is a cross-sectional view showing a configuration of a posture control unit according to a first modified example.
Figure 21:
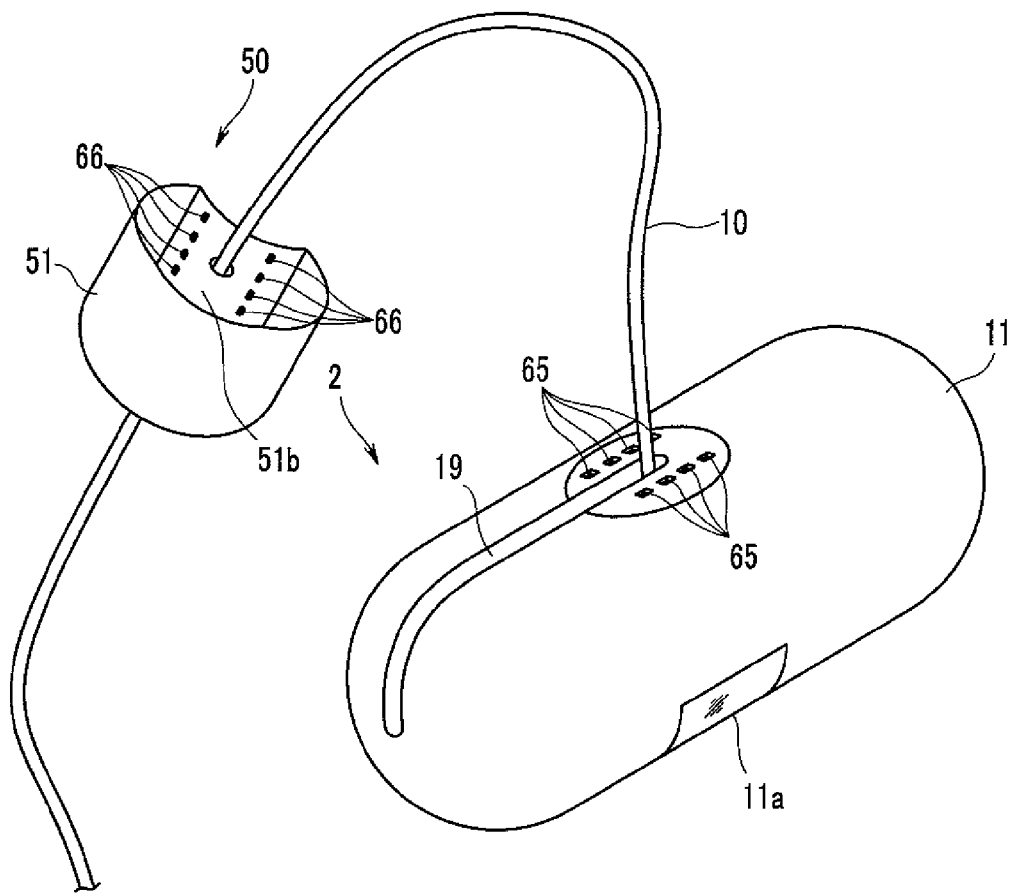
FIG. 21 relates to the second embodiment of the present invention and is a perspective view showing configurations of an intra-abdominal cavity set camera and a posture control unit according to a second modified example.

Next, the second embodiment related to the abdominal camera system according to the present invention will be described with reference to FIGS. 17 to 21. Note that FIGS. 17 to 21 relate to the second embodiment of the present invention in which: FIG. 17 is a perspective view showing configurations of an intra-abdominal cavity set camera and an observation direction control unit that are set in the abdominal cavity; FIG. 18 is a perspective view showing the configuration of the observation direction control unit; FIG. 19 is a cross-sectional view showing the configuration of the observation direction control unit; FIG. 20 is a cross-sectional view showing a configuration of an observation direction control unit according to a first modified example; and FIG. 21 is a perspective view showing configurations of an intra-abdominal cavity set camera and an observation direction control unit according to a second modified example.

In addition, in the description below, the same reference numerals are used for the same constituent elements as those in the camera system 1 according to the above-described first embodiment, and detailed descriptions of thereof will be omitted.

As shown in FIGS. 17 to 19, the abdominal camera system 1 according to the present embodiment includes an observation direction control unit 50, as an observation direction control mechanism (observation direction control means) in the present embodiment, including: a housing 51 serving both as an abdominal wall fixing section which contacts the abdominal wall 102 by pulling or relaxing operation of the operation wires 26 to 29 and as a camera fixing section; and four protrusion portions 52a to 52d which project and retract on the upper surface of the housing 51. Note that other constituent elements are the same as those in the above-described first embodiment.

The observation direction control unit 50 in the present embodiment includes the above-described housing 51 which has a substantially cylindrical shape and made of a metal rigid material, for example, and the hanging tube 4 is connected to the upper surface center of the housing 51. Note that the housing 51 has an arc surface (not shown) which is formed on the lower surface on the side of the camera 2 so as to substantially coincide with the outer shape of the main body section 11 of the camera 2 and which abuts and holds the camera 2, similarly as in the camera fixing section 21 according to the first embodiment.

The four protrusion portions 52a to 52d, which project and retract on the upper surface of the housing 51, are substantially column shaped rods, and shaft bodies 53a to 53d having a smaller diameter than that of the protrusion portions are connected to the end portions of the lower portion sides, as defined here, of the protrusion portions. The four protrusion portions 52a to 52d are disposed in four hole portions 55 which respectively open on the upper surface of the housing 51. Note that the four hole portions 55 are formed so as to be equally spaced from each other around the center of the housing 51.

In the disposed state in the respective hole portions 55, the shaft bodies 53a to 53d are inserted in bias springs 54 which are biasing members housed in the respective hole portions 55. The bias springs 54 abut the end portions of the protrusion portions 52a to 52d and bias the protrusion portions 52a to 52d upward.

In addition, the housing 51 includes a hole portion 51a communicating with the hanging tube 4. The hole portion 51a is formed so as to penetrate the housing 51 in the vertical direction at the substantially center position of the housing 51, and the wire 10 extended from the camera 2 is inserted and arranged in the hole portion 51a. Furthermore, the hole portion 51a branches from the halfway portion on the lower side in four directions equally spaced from each other around the center of the housing 51, and communicate with four wire insertion paths into which the four operation wires 26 to 29 are inserted, respectively.

As shown in FIG. 19, the four wire insertion paths which extend in the horizontal direction so as to communicate with the hole portion 51a and which are hole portions formed in an L-shape extending upward inside the housing 51. In addition, a plurality of pulleys 56 for reducing sliding resistance of the operation wires 26 to 29 in the wire insertion paths are provided at the corner portions and the opening portions on side of the hole portion 51a of the four wire insertion paths in the housing 51. The wire insertion paths communicate with the hole portions 55 in which the respective protrusion portions 52a to 52d are disposed.

The operation wires 26 to 29 are connected to the end portions of the shaft bodies 53a to 53d. Note that the shaft bodies 53a to 53d have a diameter configured so as to be advanceable/retractable in the wire insertion paths, and are guided straight in the vertical direction along the wire insertion paths.

As shown in FIG. 19, the observation direction control unit 50 configured as described above has the protrusion portions 52a to 52d configured to project and retract on the upper surface of the housing 51 by pulling or relaxing the four operation wires 26 to 29 from the extracorporeal side. Note that the respective protrusion portions 52a to 52d are subjected to a biasing force of the bias springs 54 to be pushed upward and protrude from the upper surface of the housing 51 when the operation wires 26 to 29 connected to the respective protrusion portions are relaxed.

Accordingly, in the camera system 1 according to the present embodiment, the protrusion portions 52a to 52d projected on the upper surface of the housing 51 press the abdominal wall 102 by pulling or relaxing four operation wires 26 to 29 individually, or plural wires among the four operation wires at the same time, with the camera 2 retained and fixed at the abdominal wall 102 in the abdominal cavity 101 through the observation direction control unit 50, similarly as in the first embodiment. According to such a configuration, the camera 2 is, together with the observation direction control unit 50, inclined with respect to the abdominal wall 102, and the observation (field of view) direction (direction of the photographing optical axis O) of the camera 2 is changed.

That is, also in the camera system 1 according to the present embodiment, the observation (field of view) direction of the image pickup unit 15 of the camera 2 can be easily changed in the direction desired by a user by changing the posture angle of the main body section 11 of the camera 2 in the state where the camera 2 is retained and fixed at the abdominal wall 102 in the abdominal cavity 101 through the observation direction control unit 50, by pulling or relaxing operation of the four operation wires 26 to 29.

As described above, also the camera system 1 according to the present embodiment provides the same effects as those in the first embodiment, and is capable of easily changing the observation (field of view) direction of the camera 2 set in the abdominal cavity 101 inside a body in the direction desired by the user, based on the operation of the four operation wires 26 to 29 from the extracorporeal side, and in addition, has an excellent performance of varying the observation (field of view) based on the operation.

FIRST MODIFIED EXAMPLE

As shown in FIG. 20, the observation direction control unit 50 may be configured such that the protrusion portions 52a to 52d connected to shaft bodies 61a are projected and retracted on the upper surface of the housing 51 by the four electric actuators 61 which advance and retract the shaft bodies 61a.

According to such a configuration, a control section 62, a battery 63, and a receiver 64 are disposed in the housing 51. Note that operation instruction is wirelessly outputted to the receiver 64 by a controller 60, and the four electric actuators 61 are driven by the control section 62.

SECOND MODIFIED EXAMPLE

When an electric configuration is provided in the observation direction control unit 50, as shown in FIG. 21, a plurality of electric contacts 66, which are configured to be electrically connected to a plurality of electric contacts 65 provided on the outer surface of the camera 2, may be provided on an arc surface 51b formed so as to substantially coincide with the outer shape of the main body section 11 of the camera 2.

According to such a configuration, since the four electric actuators 61 in the observation direction control unit 50 can be driven and controlled by using the electric configuration such as the control section 12 and the battery 13 in the camera 2, there is no need for a complicated structure for the observation direction control unit 50, thereby enabling the size of the observation direction control unit 50 to be reduced.
(Third Embodiment)

Next, the third embodiment related to the abdominal camera system according to the present invention will be described below with reference to FIG. 22. Note that FIG. 22 relates to the third embodiment of the present invention and is a cross-sectional view showing the configuration of the intra-abdominal cavity set camera set in the abdominal cavity.

In addition, also in the description below, the same reference numerals are used for the same constituent elements as those in the above-described first embodiment, and detailed descriptions thereof will be omitted.

Figure 22:
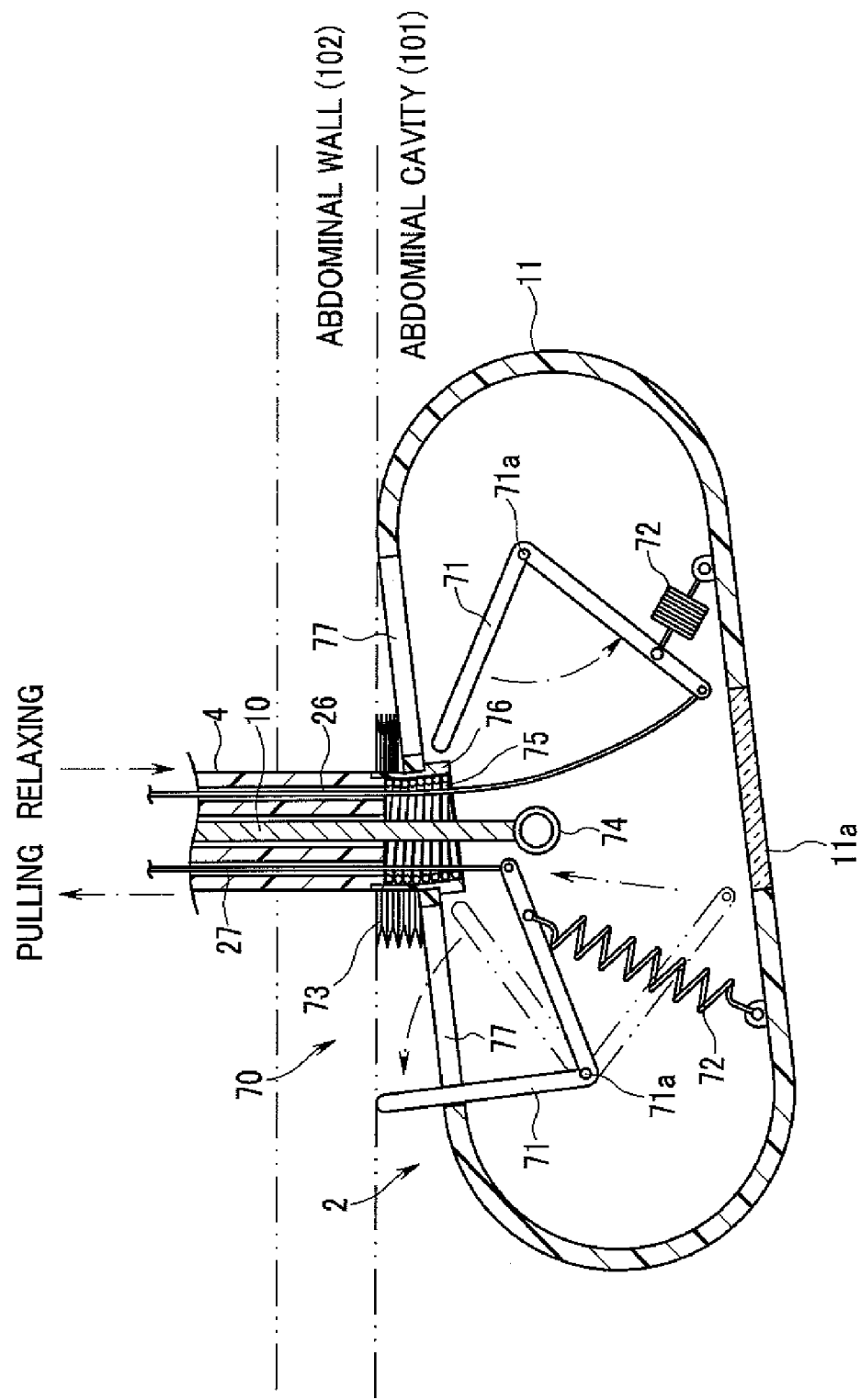
FIG. 22 relates to a third embodiment of the present invention and is a cross-sectional view showing the configuration of the intra-abdominal cavity set camera set in an abdominal cavity.

As shown in FIG. 22, the camera system 1 according to the present embodiment includes an observation direction control mechanism 70, which is observation direction control means in the present embodiment, having substantially L-shaped plate-like two link members 71 which are rotatably arranged in the main body section 11 of the camera 2 and have end portions to be projected from and retracted in a groove portion 77 formed on the upper portion of the main body section 11.

According to the specific configuration of the observation direction control mechanism 70, the two link members 71 are arranged at positions in a direction along the longitudinal direction of the main body section 11 of the camera 2, the positions being line-symmetric with respect to the lateral direction connecting the upper center and the lower center of the main body section 11. Each of the link members 71 has a flexure section pivotally supported by a rotary shaft 71a disposed in the main body section 11, and is configured to be rotatable.

In addition, the respective link members 71 have one end portions located on the lower side in the main body section 11, and the operation wires 26, 27 are connected to the one end portions. Furthermore, each of the link members 71 has a coil spring 72, one end portion of which is connected to a halfway portion between the one end portion and the rotary shaft 71a. The coil spring 72 has the other end portion connected and fixed to the lower portion of the main body section 11 and biases downward the link member 71 connected thereto.

The hanging tube 4 in the present embodiment is a multi-lumen tube as shown in FIG. 6. The hanging tube 4 is connected to the upper center of the main body section 11 of the camera 2 through a flexible tube 76 covering a coil spring 75 inside thereof. In other words, the flexible tube 76 covering the coil spring 75 is provided between the hanging tube 4 and the main body section 11 of the camera 2. The flexible tube 76 is covered with a flexible bellows tube (accordion tube) 73.

In addition, the wire 10 and the operation wires 26, 27, which are inserted and arranged in the hanging tube 4, are inserted through the coil spring 75 and extended in the main body section 11. The end portion of the wire 10, which is located in the main body section 11, is connected to a wire clamp 74 disposed in the main body section 11. According to such a configuration, the wire 10 is connected to the main body section 11 and configured to be able to haul up the camera 2. Note that, by reducing the size of the clearance between the operation wires 26, 27 and the insertion path of the hanging tube 4, the operation wires 26, 27 are subjected to sliding resistance, thereby capable of holding the advancing/retracting position of the operation wires to some extent and capable of maintaining transmission of a force to the link members 71 when the operation wires are pulled.

According to the configuration as described above, the two operation wires 26, 27 are pulled or relaxed from the extracorporeal side, thereby allowing the end portions of the link members 71 to project or retract on the upper surface through the groove portion 77 of the main body section 11. Note that the end portions of the respective link members 71, which are connected to the operation wires 26 and 27, are rotated and biased downward by the coil springs 72, thereby allowing the link members 71 to be housed inside of the main body section 11 when the operation wires 26, 27 are relaxed.

Therefore, in the camera system 1 according to the present embodiment, similarly as in the first embodiment, the end portion of the link member 71 projected on the upper surface of the main body section 11 presses the abdominal wall 102 by individually pulling or relaxing the two operation wires 26, 27, with the camera 2 retained and fixed at the abdominal wall 102 in the abdominal cavity 101. According to such a configuration, the camera 2 is inclined with respect to the abdominal wall 102, which causes the observation (field of view) direction (direction of photographing optical axis O) of the camera 2 to be changed.

That is, the camera system 1 according to the present embodiment is also capable of easily changing the observation (field of view) direction of the image pickup unit 15 of the camera 2 in a direction desired by a user by changing the posture angle of the main body section 11 of the camera 2 by pulling or relaxing the two operation wires 26, 27, with the camera 2 retained and fixed at the abdominal wall 102 in the abdominal cavity 101.

As described above, the camera system 1 according to the present embodiment also provides the same effects as those in the first embodiment, and is capable of easily changing the observation (field of view) direction of the camera 2 set in the abdominal cavity 101 inside a body in a direction desired by a user, based on the operation of the two operation wires 26, 27 from the extracorporeal side and, in addition, has an excellent response performance for varying the observation (field of view) direction based on the operation.

(Fourth Embodiment)

Next, with reference to FIGS. 23, 24, the fourth embodiment related to the abdominal camera system according to the present invention will be described below. Note that FIGS. 23 and 24 relate to the fourth embodiment of the present invention in which, FIG. 23 is a cross-sectional view showing a configuration of an intra-abdominal cavity set camera, and FIG. 24 is a cross-sectional view showing the configuration of the intra-abdominal cavity set camera set in the abdominal cavity.

In addition, also in the description below, the same reference numerals are used for the same constituent elements as those in the above-described first embodiment, and detailed descriptions thereof will be omitted.

Figure 23:
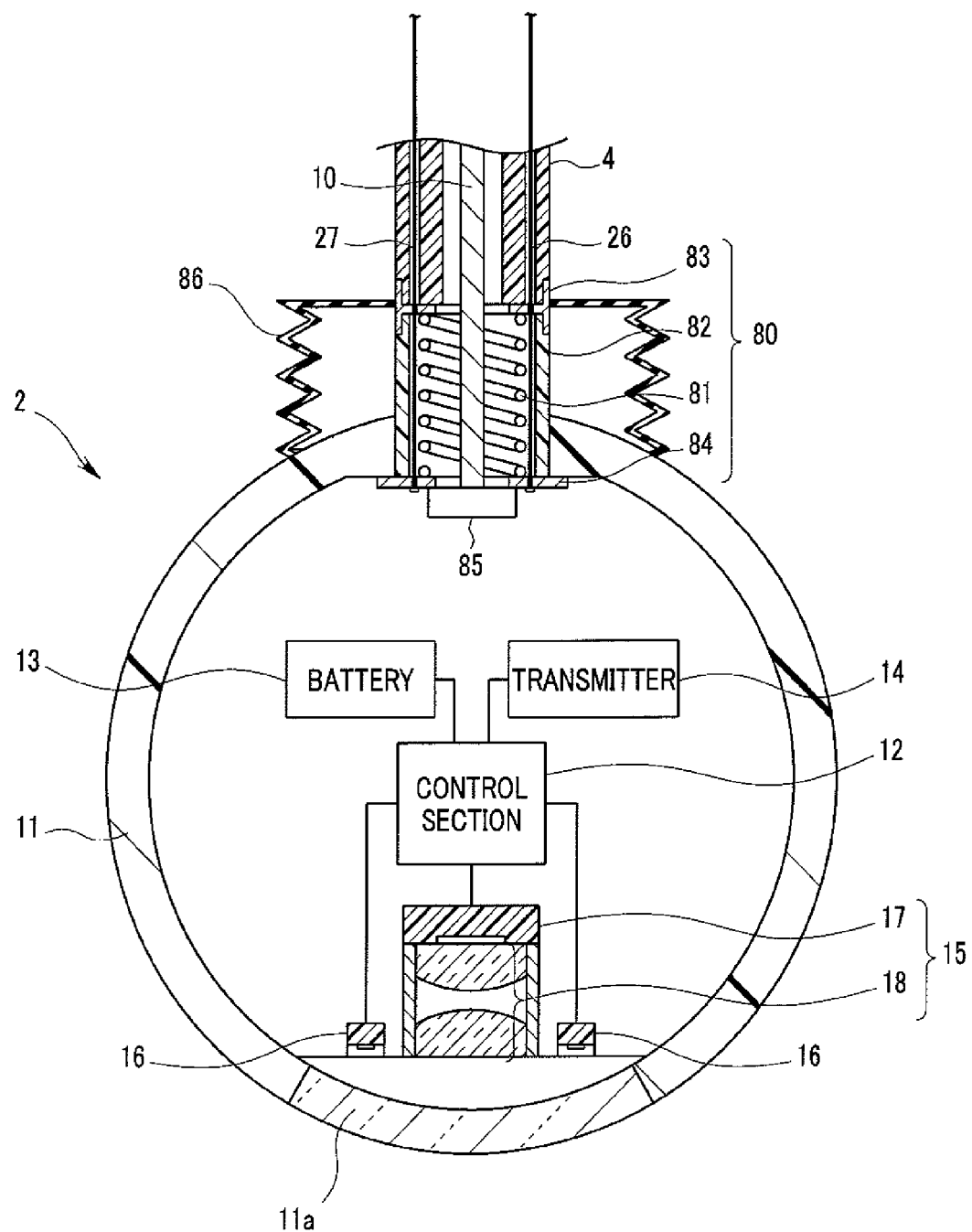
FIG. 23 relates to a fourth embodiment of the present invention and is a cross-sectional view showing a configuration of an intra-abdominal cavity set camera.
Figure 24:
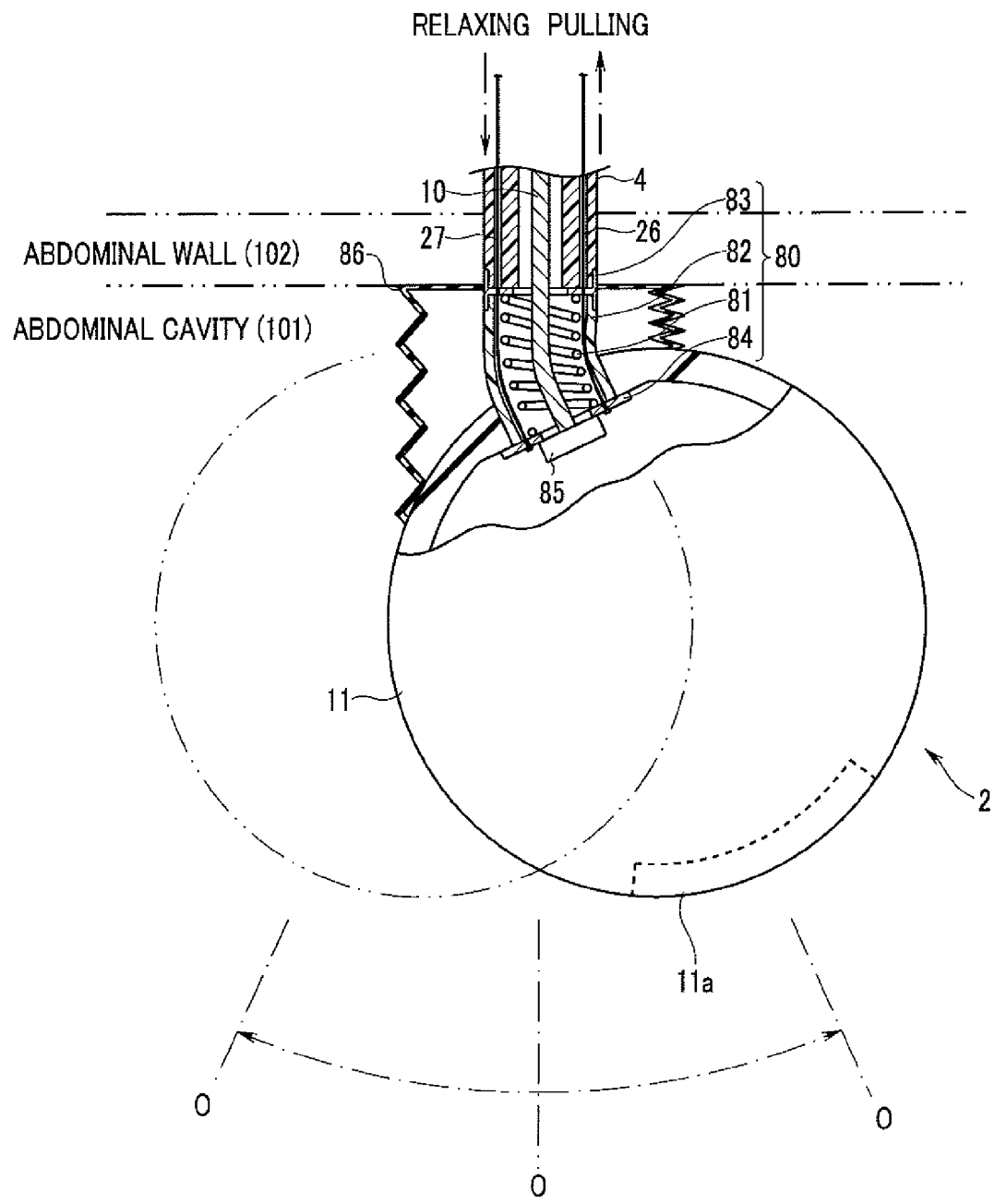
FIG. 24 relates to the fourth embodiment of the present invention and is a cross-sectional view showing the configuration of the intra-abdominal cavity set camera set in the abdominal cavity.

The camera system 1 according to the present embodiment, as shown in FIG. 23, includes an observation direction control mechanism 80, as observation direction control means in the present embodiment, which is disposed between the main body section 11 of the camera 2 and the hanging tube 4 configured as a multi-lumen tube.

The observation direction control mechanism 80 includes: a coil spring 81; a flexible tube 82 which covers the coil spring 81 and has a lower side end portion connected to the main body section 11 of the camera 2; a ring-shaped connecting member 83 which configures a connecting portion with the hanging tube 4, and an upper side spring receiver for the coil spring 81; and a washer 84 which abuts the upper side center inner surface of the main body section 11 of the camera 2 to be fixed thereto and configures a lower side spring receiver for the coil spring 81. The observation direction control mechanism 80 is covered with a flexible bellows tube (accordion tube) 86.

The wire 10 is inserted into the connecting member 83, the coil spring 81, and the washer 84, from the hanging tube 4 toward the side of the camera 2, and is connected to a wire clump 85 which abuts the washer 84 in the main body section 11.

In addition, the four operation wires 26 to 29 are inserted into the connecting member 83, and a space between the coil spring 81 and the flexible tube 82, from the hanging tube 4 toward the side of the camera 2, and are connected to the washer 84.

According to the configuration as described above, when the operation wires 26 to 29 are pulled from the extracorporeal side, the washer 84 connected to the operation wires 26 to 29 is pulled upward which is the side of the connecting member 83, against the biasing force of the coil spring 81. At this time, stress acts on the washer 84 in a direction in which the side of the pulled wire among the operation wires 26 to 29 is inclined upward. Therefore, stress acts also on the main body section 11 of the camera 2 to which the washer 84 abuts and fixed, in the direction in which the side of the pulled wire among the operation wires 26 to 29 is inclined upward.

That is, as shown in FIG. 24, in the camera system 1 according to the present embodiment, similarly as in the first embodiment, in the state where the camera 2 is retained and fixed at the abdominal wall 102 in the abdominal cavity 101, the part of the coil spring 81 on the side of the pulled operation wire 26 contracts and bent together with the flexible tube 82, which causes the camera 2 to incline with respect to the abdominal wall 102. This allows the observation (field of view) direction (direction of photographing optical axis O) of the camera 2 to be changed.

That is, the camera system 1 according to the present embodiment is also capable of easily changing the observation (field of view) direction of the image pickup unit 15 of the camera 2 in a direction desired by a user by changing the posture angle of the main body section 11 of the camera 2 with the camera 2 retained and fixed at the abdominal wall 102 in the abdominal cavity 101, by pulling or relaxing the four operation wires 26 to 29.

As described above, also the camera system 1 according to the present embodiment provides the same effects as those in the first embodiment, and is capable of easily changing the observation (field of view) direction of the camera 2 set in the abdominal cavity 101 inside a body in the direction desired by the user, based on the operation of the two operation wires 26, 27 from the extracorporeal side, and in addition, has an excellent response performance for varying the observation (field of view) direction based on the operation.

In addition, the invention described in the embodiments is not limited to the embodiments and modified examples, and various modifications are possible without departing from the gist of the invention in a practical stage. Furthermore, the above-described embodiments include inventions of various stages, and by combining a plurality of constituent components disclosed in the embodiments, inventions of various stages can also be extracted.

For example, even if some constituent components are deleted from all the constituent components shown in the above-described present embodiments, if the described problem to be solved by the invention can be solved and the effects of the invention can be obtained, the configuration in which some constituent components are deleted can be extracted as an invention.

What is claimed is:

1. A medical apparatus comprising:
    an image pickup apparatus to be introduced in a body and retained therein;
    a retaining/fixing section configured to contact a body wall in the body, for retaining and fixing the image pickup apparatus at the body wall;
    a plurality of operation wires configured to be operated from an extracorporeal side; and
    an observation direction control section for changing an observation direction of the image pickup apparatus by operation of the plurality of wires;
    wherein the observation direction control section includes:
    an image pickup apparatus fixing section configured to be connected to the operation wires and to contact an outer surface part of the image pickup apparatus;
    and a rotary section configured to support the retaining/fixing section and the image pickup apparatus fixing section so as to be separated from each other by a predetermined distance, and allow the image pickup apparatus fixing section to rotate with respect to the retaining/ fixing section with a rotation center as a fulcrum, based on the operation of the plurality of operation wires.

2. The medical apparatus according to claim 1, wherein the observation direction control section includes an elastic member connected to the image pickup apparatus, and the plurality of operation wires are connected to the elastic member and the elastic member stretches and contracts by pulling or relaxing operation of the plurality of operation wires, to thereby change the observation direction of the image pickup apparatus.

3. The medical apparatus according to claim 1, further comprising
a wire configured to be extended from the image pickup apparatus and inserted in the observation direction control section,
wherein a groove portion is formed on an exterior section of the image pickup apparatus, for housing the wire extending to the observation direction control section, when the observation direction control section is arranged at a predetermined position of the image pickup apparatus.

4. A medical apparatus comprising:
an image pickup apparatus to be introduced in a body and retained therein;
a retaining/fixing section configured to contact a body wall in the body, for retaining and fixing the image pickup apparatus at the body wall;
a plurality of operation wires configured to be operated from an extracorporeal side; and
an observation direction control section including a plurality of projectable/retractable protrusion portions respectively connected to the plurality of operation wires, the observation direction control section changing an observation direction of the image pickup apparatus by projecting and retracting the plurality of protrusion portions to bring the protrusion portions into contact with the body wall, by pulling or relaxing operation of the plurality of operation wires.

5. The medical apparatus according to claim 4, wherein the observation direction control section includes a biasing member for biasing the respective plurality of protrusion portions in a projection direction.

6. The medical apparatus according to claim 4, further comprising
a wire configured to be extended from the image pickup apparatus and inserted in the observation direction control section,
wherein a groove portion is formed on an exterior section of the image pickup apparatus, for housing the wire extending to the observation direction control section, when the observation direction control section is arranged at a predetermined position of the image pickup apparatus.

* * * * *